United States Patent [19]
Redding, Jr.

[11] Patent Number: 5,271,881
[45] Date of Patent: * Dec. 21, 1993

[54] APPARATUS AND METHOD FOR MAKING MICROCAPSULES

[76] Inventor: Bruce K. Redding, Jr., 2708 S. 86th St., Philadelphia, Pa. 19153

[*] Notice: The portion of the term of this patent subsequent to Dec. 18, 2007 has been disclaimed.

[21] Appl. No.: 628,582

[22] Filed: Dec. 17, 1990

Related U.S. Application Data

[63] Continuation-in-part of Ser. No. 187,982, Apr. 29, 1988, Pat. No. 4,978,483, which is a continuation-in-part of Ser. No. 101,802, Sep. 28, 1987, abandoned.

[51] Int. Cl.$^5$ .................... B01J 13/20; B01J 13/22
[52] U.S. Cl. .................... 264/432; 264/4.1; 264/23; 264/4; 427/213.3; 427/213.31; 427/212; 425/5; 425/804
[58] Field of Search .......... 428/402.2, 402.24; 264/4.1, 4.3, 4.32, 4.6, 4; 427/213.3, 213.31, 212; 425/5

[56] References Cited

U.S. PATENT DOCUMENTS

| | | |
|---|---|---|
| 4,452,747 | 6/1984 | Gersonde .................. 264/4.1 |
| 4,482,606 | 11/1984 | Bousquet et al. ........... 428/402.2 |
| 4,721,612 | 1/1988 | Janoff et al. ............... 264/4.1 X |
| 4,753,788 | 6/1988 | Gamble ..................... 264/4.1 X |
| 4,880,634 | 11/1989 | Speiser ..................... 424/450 |
| 4,895,452 | 1/1990 | Yiournas et al. ........... 264/4.1 X |
| 4,931,361 | 6/1990 | Baldeschwieler et al. .... 428/402.2 |
| 4,978,483 | 12/1990 | Redding, Jr. .............. 264/4.32 |

Primary Examiner—Robert L. Stoll
Assistant Examiner—John M. Covert
Attorney, Agent, or Firm—Robert S. Lipton

[57] ABSTRACT

An abrupt pressure change applied to a dispersion of core and shell material in a liquid carrier medium encapsulates the core material within the shell material. The method and apparatus of this invention permit a wider range of core and shell materials to be utilized than was possible with prior art methods including materials which previously have not been usable as shell materials. Materials in solid, liquid, gas or multiphase form may be encapsulated. Additionally, capsules are produced in a small fraction of the time required by prior art methods. The total time to perform the encapsulation may range from a few seconds to only a few minutes. The abrupt pressure change may be applied to the dispersion by either a piston or ultrasonic apparatus in both batch, semi-continuous, and continuous processes. Recycling of the capsules through the apparatuses permits adjustment of the capsules' characteristics as well as formation of multiple core capsules.

39 Claims, 10 Drawing Sheets

APPARATUS AND METHOD FOR MAKING MICROCAPSULES

This is a Continuation-in-Part of U.S. Pat. application Ser. No. 07/187,982 filed on Apr. 29, 1988, now U.S. Pat. No. 4,978,483 which is a Continuation-in-part of U.S. Pat. application Ser. No. 101,802 filed on Sept. 28, 1987 and since abandoned.

BACKGROUND OF THE INVENTION

The apparatus and method of this invention relate to the field of making capsules having a core material encased within a shell or wall material. Encapsulation is the term applied to the formation from suitable materials of a shell which encloses a core material. The capsule that is formed may have as a core material which is solid, liquid, gas, or a multi-phasic compound. This invention is concerned with capsules having sizes ranging from approximately a micron to a few millimeters. Such capsules are generally referred to as microcapsules; although that term is not specifically defined in the literature. As used herein, the terms "shell" and "wall" are used interchangeably to denote the barrier surrounding the core material separating it from the environment.

Capsules and/or microcapsules need not be uniformly spherical but may consist of irregularly-shaped objects such as those having a shell surrounding an irregular shaped solid crystalline core. A capsule core may be a single solid crystal, a chemical compound, an emulsion, a liquid, a mixture of different solid materials or other suspensions, or it may be a combination of smaller capsules. The shell or wall may likewise be complex having multiple walls of different composition. Thus, it is possible to have a first capsule having its own core and shell which forms the core for a second capsule having a shell formed from the same or a different material.

Capsules have been developed to serve a variety of functions. One general purpose of encapsulation is to preserve or isolate the core material from its environment until an appropriate time or condition is present. In these situations, the core material is protected from the environment by the shell. Such protection is not always easily achieved since the core material may be able to penetrate or diffuse through the shell. On the other hand, use can be made of the "leaky" feature of some shells to control the release rate of the core material into the surrounding environment.

Encapsulation can also be used to protect compounds from environmental conditions such as temperature, pH, or chemically reactive surroundings such as oxidizing and reducing environments. Such oxidizing and reducing environments may consist of chemicals to which the capsule has been added. In other cases, it is desirable to encapsulate certain chemical compounds not only for protection of the core but also to protect or shield the external environment from reaction with the chemical compound forming the core. One common example of this use for encapsulation is the masking of the taste and/or odor of a chemical composition. In such a case, encapsulation may offer protection against detection of a bitter, toxic or otherwise undesirable taste or odor. Encapsulation of skin and respiratory irritants and toxins is one important way to protect the handlers of such materials from exposure.

During the past two decades, encapsulation of a broad range of materials has been achieved using a variety of encapsulation techniques. Capsules have found use in many applications such as in the manufacture of pharmaceuticals, pesticides, paints, adhesives and many other chemical products. To date, the most widely-known use of microcapsules has been in the product generally known as "carbonless paper". In carbonless paper, microcapsules provide a controlled release of a color forming reagent core. The forming agent is released from carbonless paper microcapsules when applied pressure ruptures the capsule walls. The agent then reacts with another dye forming member on the paper beneath to create an image.

Examples of processes for forming microcapsules are given in Vandegaer, "Microencapsulation Processes and Applications," Plenum Press, New York, 1974, M. Gutcho, "Microcapsules and other Capsules", Chemical Technology Review, No. 135, Noyles Data Service, Park Ridge, N.J. 1979, and the Kirk-Othmer Encyclopedia of Chemical Technology, 3rd Edition (1981), volume 15. Other references disclosing processes for forming microcapsules include U.S. Pat. Nos. 3,943,063; 3,460,972, 4,001,140; and 4,087,376.

The above-mentioned references describe several liquid-phase methods of encapsulation. These methods include coacervation, thermal coacervation, complex coacervation, interfacial polymerization, and others. In the process of coacervation, the core and shell materials are mixed together in a liquid medium. When the core and shell materials have been agitated for a sufficient period of time, portions of the core material become coated with shell material, thus forming capsules within the liquid medium. The size of these capsules is controlled by the speed and design of the mixing element within the vessel. The thickness of the shell material is adjusted by a further chemical treatment process.

FIG. 1 shows the process of coacervation, which is a liquid-phase microencapsulation process of the prior art. The details of this method are described in U.S. Pat. No. 2,800,457. In the method shown in FIG. 1, an oily substance, which comprises the core of the microcapsule, is dispersed in an aqueous solution of gelable hydrophilic colloid materials. The hydrophilic colloid materials, which become the shell of the capsules, are made to coagulate when the core material and the colloid materials are agitated within the aqueous carrier. Eventually, the emulsified droplets of the oily substance become coated with the colloid material, as the latter forms a solid wall or shell around each droplet. The capsules formed in this manner may be used in the liquid medium, or may be dried to a fine powder form.

Variations in the coacervation process have been developed. For example, polymers have been used as shell materials. It is possible to adjust the pH of the mixture to cross-link and harden the shell. However, both the method described above and its variations have disadvantages. A principal disadvantage of the prior art processes is the amount of time required to form capsules. The time consumed by a typical coacervation process is illustrated in FIG. 2. FIG. 2 shows the time required to complete the three major stages in capsule formation. As shown in FIG. 2, it takes about one hour to form "pre-capsules," i.e. newly-formed capsules which have very thin shells, and which need further hardening before they can survive in the outside environment. Microdispersions are examples of such materials. At this stage, the capsule walls occupy less than 5% of the volume of the capsules.

An additional two hours or more may be required to reach the second stage, wherein the shell is completely formed. At this point, additional layers of shell material are deposited onto the initial shell. In this second stage, the wall volume may be increased from 5% to above 90% of the total volume of the capsule, depending upon the duration of agitation, the level of turbulence of the agitation, and the concentration of shell material in the mixture.

The third stage of capsule formation, in the coacervation process, may require yet another 1-2 hours. In this stage, the shell is hardened into its final form. The hardening is often accomplished by cross-linking the shell material. The cross-linking is often induced chemically, or by adjusting the temperature of the completed capsules. Thus, as shown in FIG. 2, the time required for the entire coacervation process is several hours.

Listed below in Table 1 are the major encapsulation techniques of the prior art, showing the range of capsule sizes attainable with each technique, and indicating the phases of core materials which can be encapsulated with each technique. Coacervation has been described earlier. The other methods listed are described in Volume 15 of the Encyclopedia of Chemical Technology (1981), cited above, at pages 472-484.

TABLE 1

MICROENCAPSULATION: PROCESS LIMITS

| PROCESS | CORE MATERIAL | SIZE ($\mu$) |
|---|---|---|
| COACERVATION | SOLID/LIQUID | 10-500 |
| INTERFACIAL ADDITION AND CONDENSATION | SOLID/LIQUID | 5-2000 |
| AIR SUSPENSION | SOLID | 50-5000 |
| CENTRIFUGAL EXTRUSION | SOLID/LIQUID | 250-3000 |
| SPRAY DRYING | SOLID/LIQUID | 5-500 |
| PAN COATING | SOLID | 500-5000 |

Table 2 below lists some of the materials which can be encapsulated. However, this list is indicative only and is not meant to be inclusive.

TABLE 2

MATERIALS WHICH CAN BE ENCAPSULATED

| | | |
|---|---|---|
| Activated carbons | Enzymes | Pesticides |
| Adhesives | Flame retardants | Pharmaceuticals |
| Amines | Flavors | Pigments |
| Amino acids products | Food ingredients | Reflective |
| Animal feed ingredients | Fumigants | Resins |
| Antibiotics agents | Inorganic salts | Resin-curing |
| Antiseptics | Ion-exchange resins | Retinoids |
| Aqueous solutions | Liquid hydrocarbons | Sealants |
| Catalysts | Oils (vegetable) | Sterilants |
| Chemoluminescents | Organometallic compounds | Steroids |
| Chlorinated hydrocarbons | Oxidizers | Vitamins |
| Corrosion inhibitors | Perfumes | Water |
| Deodorants | Peroxides | |

The coacervation process described above has many disadvantages. It is difficult to achieve precise control of the size of the microcapsules. Inadequate agitation of the mixture frequently produces capsules which are too large, often beyond the size range suitable for the desired application. It is also difficult to adjust the thickness of the shell of the capsules. A thicker shell is often essential to enhance the shear and impact resistance of the capsule, and to enable the capsule to withstand high temperatures. In addition to these disadvantages, the coacervation process is also very time-consuming. The core and shell materials must be stirred for a long period of time, on the order of several hours, before usable capsules are produced. The time required to form the capsules adds significantly to the cost of their manufacture.

Conventional liquid-phase methods of making capsules, such as the coacervation process, often produce unsatisfactory quantities of encapsulated products. Moreover, it often happens that the core material is soluble in the liquid medium in which the shell is formed, in which case such materials dissolve in the liquid medium long before encapsulation can occur. There is presently a great demand for capsules which can be inexpensively manufactured, and which are suitable for various industrial applications.

Capsules used in industry must exhibit the following properties:
1. The capsules must be capable of withstanding large shear forces, or other stressful conditions, when the capsules are added to a host material. Suitable host materials could be paints, plastics, foam products, building materials, paper products and others. Each host material requires varying conditions of heat and stress to produce the final product, and the capsules must have suitable physical properties to enable the capsules to be used during the manufacture of the final product.
2. Capsules used in industry must generally be very small. Microcapsules made by conventional liquid-phase methods of encapsulation, and by other methods, usually have an unacceptably wide size distribution, and are often too large for use in industrial processing.
3. Capsules used in industry should be produced in a continuous process, so that the capsules are available in large quantities, and at relatively low cost.

The present invention provides a process and apparatus for making capsules which have the properties described above. The process of the present invention can produce capsules in a small fraction of the time required by conventional methods. The present invention also permits the accurate adjustment of the size of the capsules and the thickness of their shells.

SUMMARY OF THE INVENTION

Applicant has discovered an entirely new method and apparatus for producing capsules which does not limit the range of core and shell materials which may be used in the encapsulation process and allows the use in an encapsulation process of core materials and shell materials not usable with prior art processes. In addition, the time of encapsulation is reduced by the method and apparatus of this invention from several hours to either a few minutes or a few seconds. According to the method of this invention, core material and shell material are dispersed in a liquid carrier medium. The liquid carrier medium may be the same medium used to dissolve or partially dissolve the shell material or it may be another medium. An abrupt pressure change is applied to the dispersion of core and shell materials which causes the shell material to envelope and encapsulate the dispersed core material. The underlying physical mechanism is by which an abrupt pressure change causes the encapsulation is not well understood. It is suggested that pressure shock waves, shear forces, and cavitation effects resulting from the abrupt pressure change may be the operative mechanism. However, there may be other mechanisms involved.

Whatever the mechanism, the discovery that an abrupt pressure change applied to a dispersion of core and shell results in encapsulation represents a significant advance in the art of encapsulation technology. In addition the size of the capsules can be adjusted by regulating the magnitude of the abrupt pressure change. The capsules formed by the method of this invention may be recycled by using the method of the invention to alter the characteristics of the encapsulating shell, the nature of the finished capsule, as well as the final capsule size. Thus, the shell wall may be strengthened, made less porous, or constructed of multiple shell materials quickly and easily by the method of this invention. Additionally, the method permits the use of previously formed shells along with additional core materials as the core of a second generation capsule. By this technique, capsules within capsules within multiple shell walls may be constructed. Two apparatuses are provided which may be used to apply an abrupt pressure change to the dispersion. In the first apparatus, a hydraulic piston is driven against the liquid carrier medium in which the core and shell materials are dispersed so that a compressive force is applied to the medium. The release of the force from the medium may provide yet another abrupt pressure change. In a second apparatus, ultrasound is applied to the liquid medium containing the dispersion of shell and core material. It is believed that the bursting of the resulting cavitation bubbles produces a localized abrupt pressure change which causes the encapsulation.

Therefore, it is the first object of this invention to provide an encapsulation method which utilizes an abrupt pressure change applied to a dispersion of core and shell material.

A further object of this invention is to provide a method whereby the walls of capsules, which are formed by the application of an abrupt pressure change to a dispersion of core and shell material, may be further modified by a subsequent abrupt pressure change applied to a dispersion of the previously formed capsules and additional shell material, which shell material may be of either of the same composition or a different composition than the shell material used to initially form the capsules.

It is an additional object of this invention to provide a method by which capsules formed by the application of an abrupt pressure change to a dispersion of core and shell material may be further utilized, themselves, as additional cores in conjunction with other core materials to form multi-cored capsules.

An additional object of this invention is to provide a piston apparatus suitable for applying an abrupt pressure change to a dispersion of core and shell materials to cause encapsulation.

An additional object of this invention is to provide an apparatus which will stabilize the capsules produced by the above-referenced piston apparatus.

Another additional object of this invention is to provide an ultrasonic apparatus which may be used to apply an abrupt pressure change to a dispersion of core and shell material to produce capsules.

It is the further object of this invention to provide a method and apparatuses for encapsulation which produce capsules in much less time than the prior art processes.

It is another object of the invention to increase greatly the speed of production of capsules.

It is another object of the invention to improve conventional liquid-phase methods of encapsulation by using the method and apparatus of this invention to complete or adjust the encapsulation process.

It is another object of the invention to reduce substantially the cost of producing capsules.

It is another object of the invention to provide a method of making microcapsules wherein the thickness of the shells of the microcapsules can be easily adjusted, and wherein the microcapsules can be made sufficiently strong to withstand large stresses.

A further object of this invention is to provide an encapsulation method whereby the size of capsules may be easily adjusted.

It is another object of the invention to provide a method of repairing malformed capsules.

Other advantages and objects of the method and apparatuses of this invention will become apparent from the description of the preferred embodiment which follows.

BRIEF DESCRIPTION OF THE DRAWINGS

FIGS. 6 and 6A show schematic cross sections of the baffled chamber shown in FIG. 5.

DETAILED DESCRIPTION OF THE PREFERRED EMBODIMENT

Figure 1:
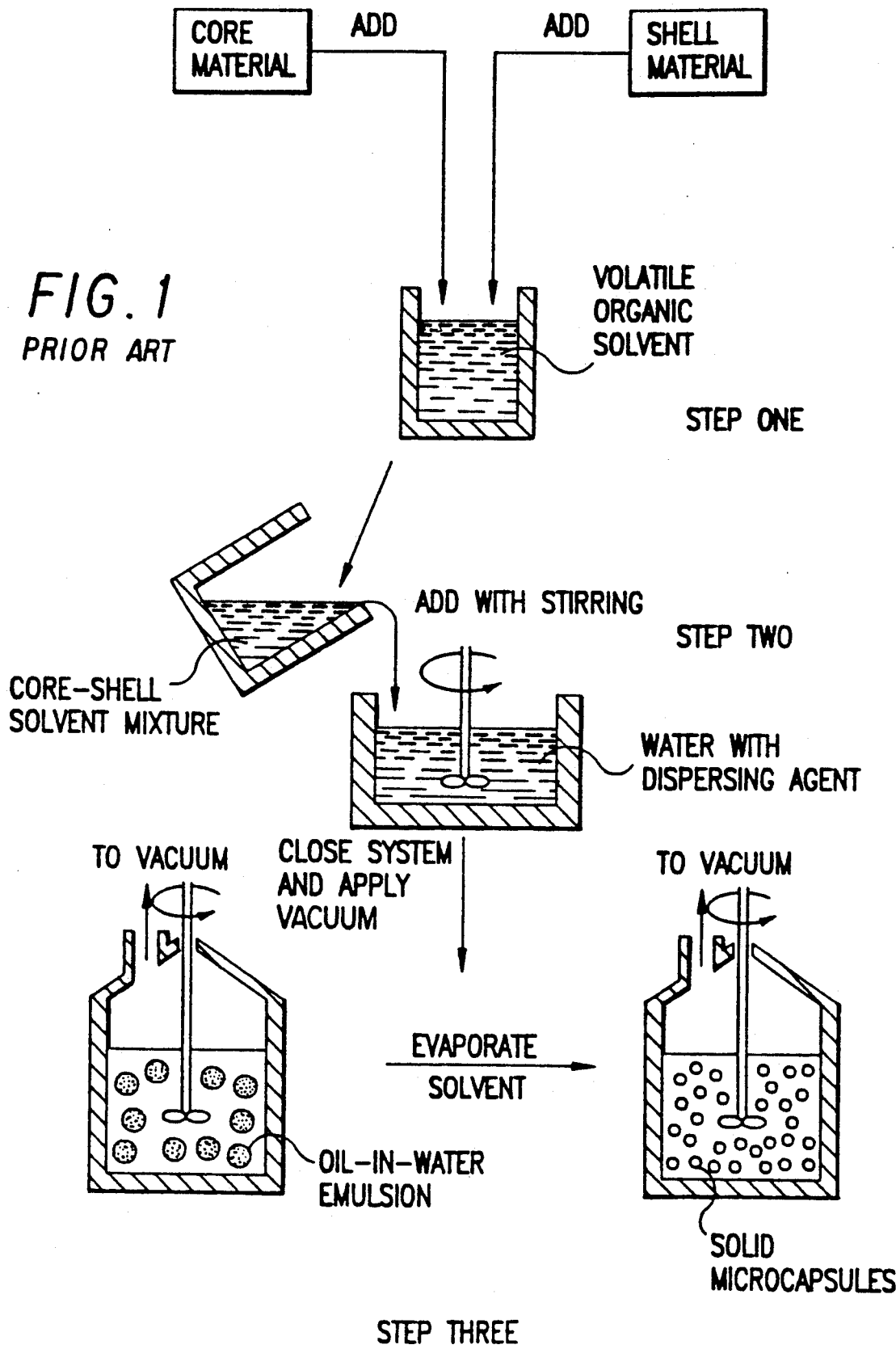
FIG. 1 is a diagram illustrating the process of coacervation, which is one of the methods used in the prior art, to form microcapsules.
Figure 2:
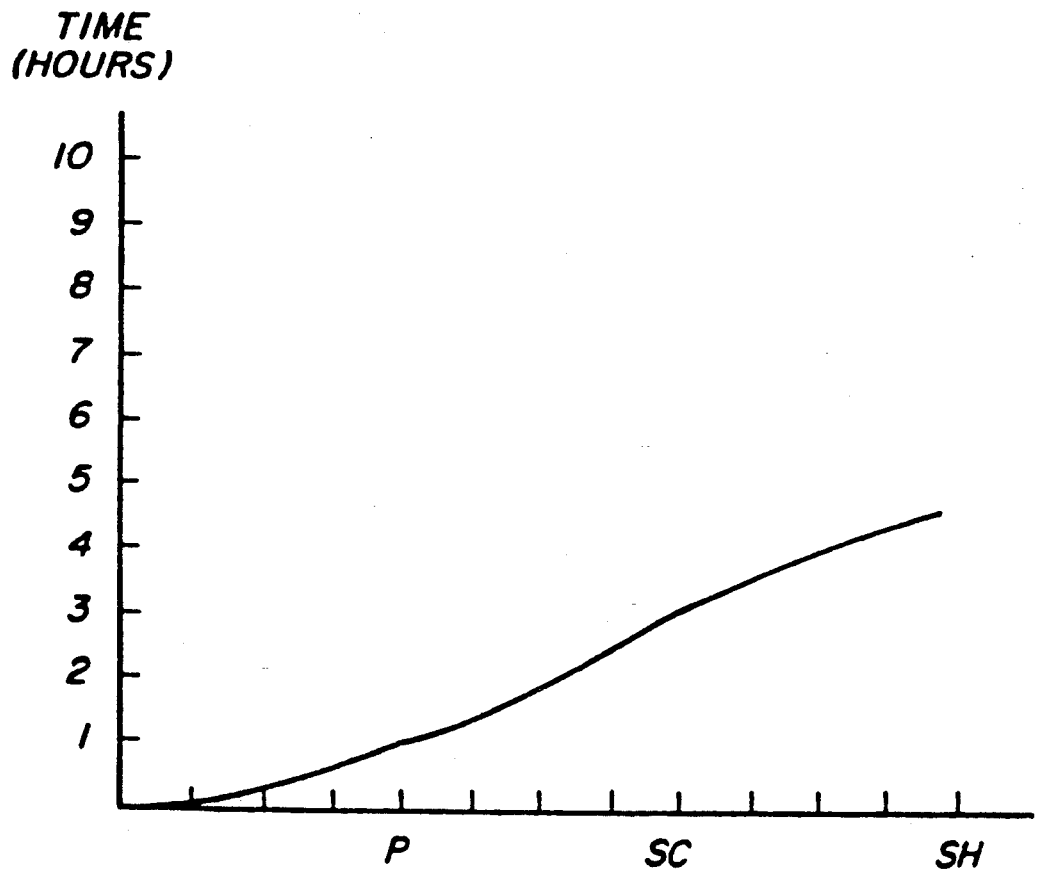
FIG. 2 is a graph showing the stages of the coacervation process illustrated in FIG. 1.

The method and apparatus of this invention are based upon the discovery that an abrupt pressure change applied to a liquid medium containing a dispersion of a core material and a shell material causes the shell material to surround and encapsulate the core material. This phenomena is unknown in the prior art of encapsulation. The core material may consist of a solid, liquid, gas, or a slurry or other dispersion of solid material in liquid. The core material may be either soluble or insoluble in the liquid medium. If the core material is a liquid, the "core" liquid must have a density or viscosity which is different from the density or viscosity of the surrounding liquid medium. Generally, any material which retains its shape and configuration in a liquid medium can be used as a core material with the method and apparatus of this invention. As will be discussed more fully later, capsules formed by prior art methods, such as coacervation, may also be used as core materials in this invention, and capsules formed by the method of this invention may be recycled and used as core material.

The shell material may consist of any of the commonly-known shell materials used in prior art processes including those which are said to form films upon dissolution in solvent as well as those which are said to be colloidal in nature and bloom into gelatinous masses in the proper solvent. In addition, it is possible to use as shell materials those materials which are not suitable for use as shell material by methods known in the prior art. Table 3 lists some typical shell materials which may be used with the method of the present invention. This table is meant to be representative, however, and not inclusive.

TABLE 3
SOME MICROENCAPSULATION MATRIX AND WALL CHEMICALS

| Natural Polymers | |
|---|---|
| Carboxymethylcellulose | Zein |
| Cellulose acetate phthalate | Nitrocellulose |
| Ethylcellulose | Propylhydroxycellulose |
| Gelatin | Shellac |
| Gum arabic | Succinylated gelatin |
| Starch | Waxes, paraffin |
| Bark | Proteins |
| Methylcellulose | Kraft lignin |
| Arabinogalactan | Natural rubber |

| Synthetic Polymers | |
|---|---|
| Polyvinyl alcohol | Polyvinyidene chloride |
| Polyethylene | Polyvinyl chloride |
| Polypropylene | Polyacrylate |
| Polystyrene | Polyacrylonitrile |
| Polyacrylamide | Chlorinated polyethylene |
| Polyether | Acetal copolymer |
| Polyester | Polyurethane |
| Polyamide | Polyvinylpyrrolidone |
| Polyurea | Poly(p-xylylene) |
| Epoxy | Polymethyl methacrylate |
| Ethylene-vinyl acetate copolymer | Polyhydroxyethyl methacrylate |
| Polyvinyl acetate | |

| Synthetic Elastomers | |
|---|---|
| Polybutadiene | Acrylonitrile |
| Polyisoprene | Nitrile |
| Neoprene | Butyl rubber |
| Chloroprene | Polysiloxane |
| Styrene-butadiene rubber | Hydrin rubber |
| Silicone rubber | Ethylene-propylene-diene terpolymer |

The actual mechanism by which abrupt pressure changes applied to a dispersion within a liquid medium cause capsules to form is not entirely understood. It is possible that the pressure shock waves created in the liquid medium by the abrupt pressure changes are directly responsible for the formation of capsules. However, it is also possible that the abrupt pressure changes and/or the pressure shock waves generate shear forces, at the interface of the core and surrounding shell containing liquid medium, which cause the shell material to surround and encapsulate the core material. It is also possible that the abrupt pressure changes and/or the pressure shock waves produce cavitation within the liquid medium, and that it is the cavitation or its consequences which induces the shell material to encapsulate the core material. Finally, it is possible that localized temperature changes and/or gradients caused by the abrupt pressure changes, pressure shock waves, shear forces or cavitation actually induce the shell material to surround and encapsulate the core material. Whatever the precise mechanism of action may be by which abrupt pressure changes work on a dispersion within a liquid medium at the interface between the core and shell materials, the formation of the resulting capsules represents a new and unanticipated advance in the art of encapsulation.

Figure 3:
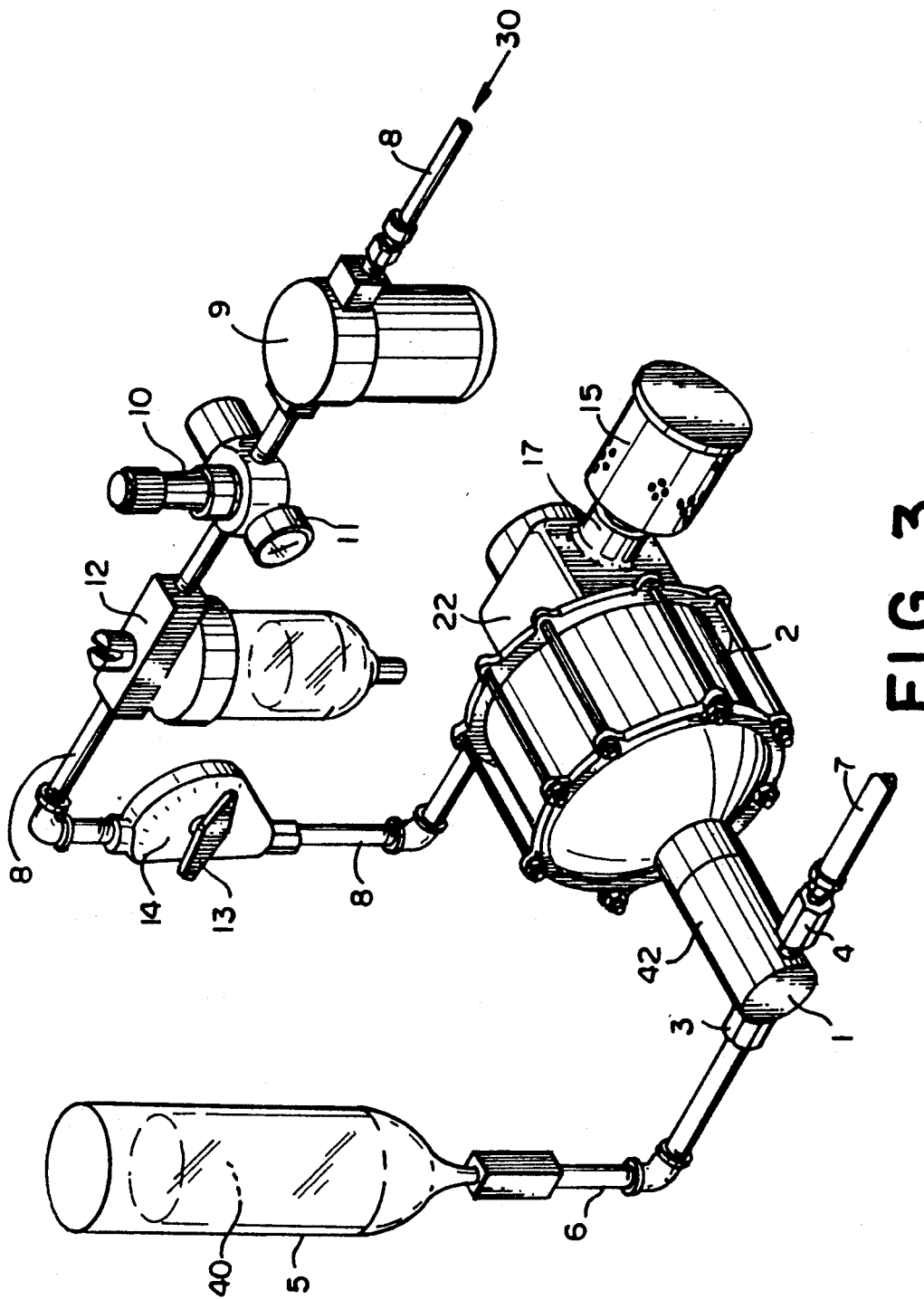
FIG. 3 shows a piston apparatus for making capsules.

Applicant has designed two apparatuses which produce capsules by the application of abrupt changes in pressure to a liquid medium containing a dispersion of core and shell materials. FIG. 3 shows a piston apparatus in which abrupt pressure changes are applied by the action of a piston striking/compressing the liquid medium containing the dispersion of core and shell followed by a release of the compression. The piston apparatus consists of a feed reservoir 5 in which is placed a dispersion of core and shell material in a liquid medium 40. Feed reservoir 5 is connected to one end of inlet line 6. The other end of inlet line 6 is connected to inlet valve 3. Inlet valve 3 leads into compression head 1. Pneumatic Pump 2 is connected to compression head 1 so that it may drive a piston 20 (not shown) towards a compression chamber 18 (not shown) within compression head 1.

Pump 2 is shown with an isolator attachment 42 mounted between the pneumatic pump 2 and the compression head 1. The isolator attachment 42 prevents any contamination from the air motor 22 from reaching the compression chamber since the hydraulic piston is not withdrawn all the way into the air motor 22 when the isolator attachment is used. Use of the isolator attachment prevents any foreign materials which may be carried in the air stream to the air motor or any of the oil used to lubricate the air motor from contaminating the liquid medium containing the dispersion of core and shell material within the compression chamber. However, the isolator does not affect the performance characteristics of the pneumatic pump in any manner nor the pressures generated within compression head 1.

Pneumatic pump 2 is driven by high pressure air 30 supplied in air line 8. A series of air conditioners are incorporated along air line 8. The first conditioner is air bleeder 9 which removes water from the compressed air. Air line 8 is next connected to pressure regulator 10 which is used to set the initial pressure adjustment of the supply air to be applied to pneumatic pump 2. Attached to pressure regulator 10 is a pressure indicating mechanism 11. After pressure regulator 10, air line 8 passes through an oiler 12 which adds oil to the compressed air to lubricate pneumatic pump 2. From oiler 12, air line 8 passes through a quarter turn bleeder valve 13. Bleeder valve 13 provides for adjustment of the air pressure supplied to pump 2 over a range from zero (0) pounds per square inch up to the pressure set by pressure regulator 10. The relative position of bleeder valve 13 is indicated by scale 14 located behind bleeder valve 13.

By installing bleeder valve 13 in the pump inlet air supply line 8, it is possible to regulate the cycling frequency of the pneumatic pump by adjusting the pump input pressure. The table below shows a typical range of cycling frequencies of pump 2 as a function of the position of quarter-turn bleeder valve 13 as it is rotated between its fully open (dial setting 0) and fully closed (dial setting 9) position. The numbers correspond to equal angular increments throughout the 90 degree rotation of the valve. The air pressure supplied to valve 13 as set at regulator 10 was 85 psig. No entries are shown for dial settings 0, 1, and 2 because the pump did not work satisfactorily at those settings.

| Dial Setting | Speed Settings Number of Cycles Per Minute | Cycle Time in Seconds |
| --- | --- | --- |
| 3 | 162 | 0.37 |
| 4 | 168 | 0.36 |
| 5 | 252 | 0.24 |
| 6 | 264 | 0.23 |
| 7 | 324 | 0.19 |
| 8 | 342 | 0.18 |
| 9 | 348 | 0.17 |

Finally, air line 8 enters inlet port 16 (not shown) of pneumatic pump motor 22. Attached to exhaust port 17 of pneumatic pump motor 22 is an air muffler 15. Exiting compression head 1 is exit valve 4 to which is connected capsule discharge line 7. Reservoir 5 and inlet line 6 may be heated, if necessary, to maintain the temperature of the core and shell dispersion prior to processing. Similarly, capsule discharge line 7 may be heated if necessary.

Figure 4:
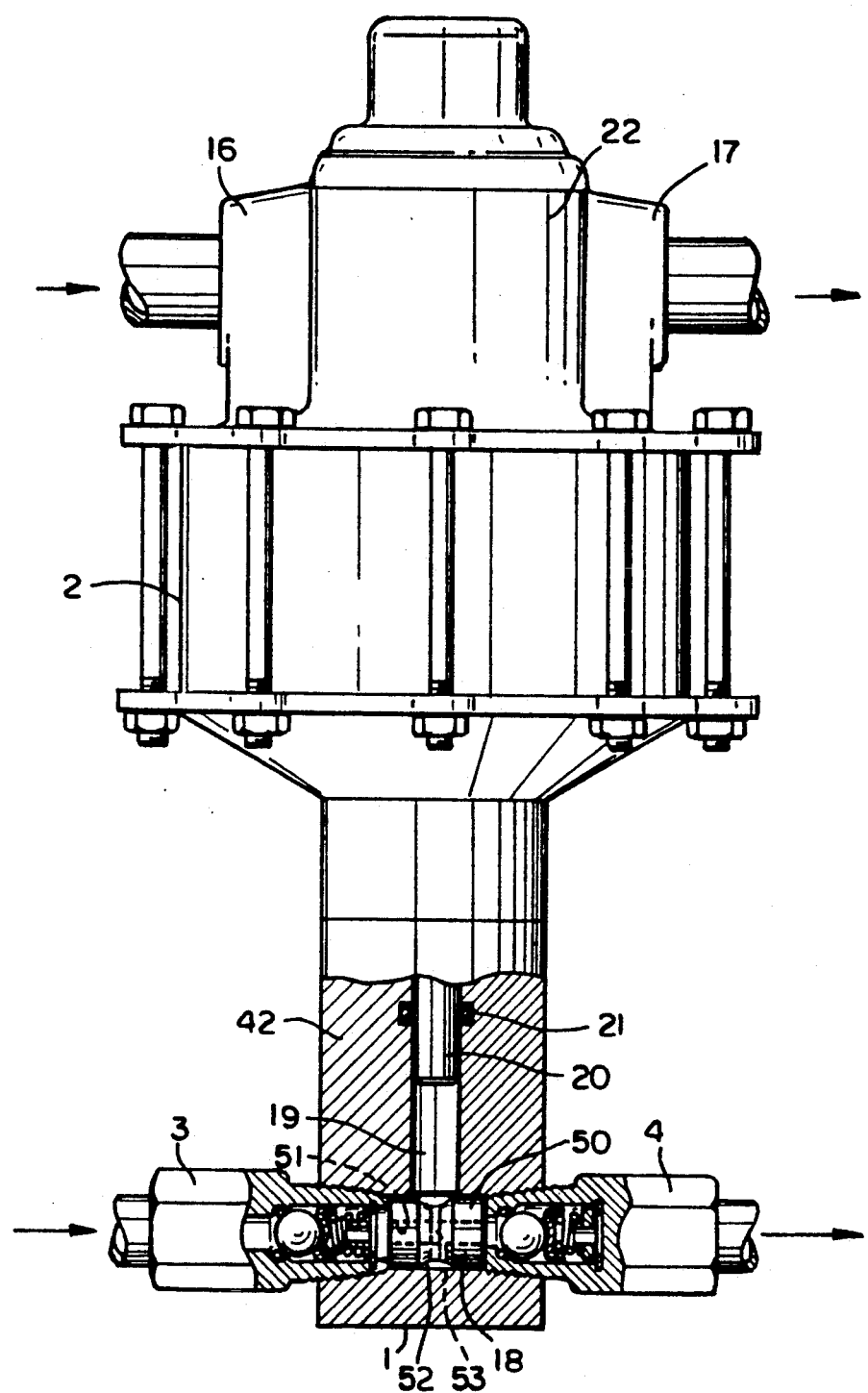
FIG. 4 shows the pneumatic pump, partially cut away, shown in FIG. 1.

FIG. 4 shows a cross-section of pneumatic pump 2 and compression head 1 viewed from above. Compression head 1 has within it a compression chamber 18. Inlet and outlet valves 3 and 4 are located at the two ends of compression chamber 18. When compressed air is supplied to pneumatic pump motor 22, piston 20 is driven down piston race 19 towards compression chamber 18 by pump motor 22. At the end of the downward stroke of piston 20, pump motor 22 changes the direction of movement of piston 20 and retracts piston 20 back to its beginning position. Piston seal 21 in isolator attachment 42 isolates pump motor 22 from compression chamber 18. All other factors remaining the same, the greater the air pressure supplied to motor pump 22, the greater the force exerted by the piston 20, and the faster (completed piston stroke cycles per minute) pump 2 cycles.

Within compression chamber 18 is volume reducing plug 50. Plug 50 consists of a solid cylinder occupying the compression chamber between valves 3 and 4. Plug 50 has a hole 51 along the length of its longer cylinder axis effectively providing an inner-compression chamber within 50 of reduced volume. Approximately midway along the length of reducing plug 50, there is an arcuate undercut groove 52 encircling plug 50. There is further provided a transverse hole 53 across the diameter of plug 50 centered on grove 52. Hole 53 starts on one side of undercut groove 52, runs through and crosses hole 51 in plug 50, and then exits in undercut groove 52 on the opposite side of plug 50. Thus holes 51 and 53 are at right angles to each other.

When reducing plug 50 is inserted in compression chamber 18, the chamber formed by hole 51 communicates with the chamber occupied by the withdrawing piston by means of transverse hole 53 and undercut groove 52. Reducing plug 50 reduces the effective volume of liquid which is subjected to the abrupt pressure change produced by the piston. Thus, as piston 20 begins to withdraw from its most extended position, liquid is drawn into the chamber formed by hole 51 and is further drawn through hole 53 into the chamber formed by undercut groove 52 around the plug and thence into the chamber formed by the piston race 19.

As indicated, pneumatic pump motor 22 is driven by high pressure air supplied through inlet port 16 which is exhausted to muffler 15 through exhaust port 17. However, a pump motor powered by any means, mechanical, electrical, pneumatic, etc., which can generate a sufficient abrupt pressure change to form capsules may be used to drive piston 20. Valves 3 and 4 are shown as check valves but they may also be solenoid-controlled valves or manually-operated valves. In the preferred embodiment, it has been found that check valves provide a convenient mode of operation permitting continuous operation of the pump. However, the spring tension in exit valve 4 must be adjusted to permit the exit of the compressed liquid dispersion from compression chamber 18 only after sufficient pressure has been applied to create the abrupt pressure change.

In order to form capsules by the method of this invention, a dispersion 40 of core and shell materials in a liquid medium is first placed in reservoir 5. The shell material may be prepared by one of the many methods known in the prior art. For instance, if a gelatinous-based shell is to be used, it may be bloomed after being dissolved in water. Other shell compounds may be dissolved in their appropriate solvent. Generally, the core material would be dispersed in the liquid medium which serves as a solvent for the shell material. However, this is not absolutely necessary, and the shell material in its solvent may be mixed with the core to form a dispersion and then placed in yet another liquid "carrier" medium.

The mixing of the shell and core material to form the dispersion, or a micro-dispersed state, may be accomplished by any of the conventionally known apparatuses including those known as batch mixers, static mixers, motionless mixtures, and fluidization equipment. The core and shell materials should be adequately mixed to form a fairly homogenous dispersion of the core and shell materials in the liquid carrier medium. The micro-dispersion is, on a macroscopic level, generally homogeneous, though not perfectly so.

Once the dispersion of core and shell materials is placed in reservoir 5, it may be conveniently fed under the force of gravity to inlet valve 3. Initially, inlet valve 3 is opened and exit valve 4 is closed permitting the dispersion of core and shell material to flow into compression chamber 18. Inlet valve 3 is then closed and high pressure air 30 supplied to pneumatic motor 22 drives piston 20 towards compression chamber 18 containing plug 50 thereby applying an abrupt pressure change to the dispersion of core and shell material contained within chambers 51, 52, and 53 all within compression chamber 18. One or several stroke cycles, consisting of a compression followed by a rarefaction stroke, of piston 20 may be applied to the dispersion of core and shell in compression chamber 18 before exit valve 4 is opened. The impact and withdrawal of piston 20 upon the virtually non-compressible material in compression chamber 18 produces abrupt pressure changes resulting in pressure shock waves, shear forces, and, perhaps, cavitation within the liquid medium in compression chamber 18. After the dispersion is subjected to these forces by the cycling of piston 20, exit valve 4 is opened and the liquid medium flows out of compression chamber 18 into capsule discharge line 7.

In the preferred embodiment, check valves are employed as valves 3 and 4. The valve action may be adjusted to provide a semi-continuous flow of capsules. As pneumatic pump motor 22 raises piston 20 after its compression stroke, the pressure within compression chamber 18 drops below the ambient air pressure on the dispersion in reservoir 5 and inlet line 6. Check valve 4 remains closed preventing previously-treated capsule containing dispersion from re-entering chamber 18 while check valve 3 opens permitting the piston to draw the liquid medium containing the dispersion of core and shell materials through holes 51 and 53 around grove 52 and into race 19. As piston 20 begins its compression stroke, check valve 3 closes thereby allowing pressure to begin to build up within compression chamber 18. The dispersion is subjected to the abrupt pressure change created as the piston begins its compression stroke. The spring in check valve 4 is set to open valve 4 approximately as the maximum pressure within the chamber is reached. When the pressure on the liquid medium generated by the compressing piston 20 exceeds the pressure setting of check valve 4, valve 4 opens permitting the liquid medium to flow out of compression chamber 18 into capsule discharge line 7. In the piston apparatus shown in FIG. 3, the pressurized liquid within compression chamber 18 is vented at atmospheric pressure into capsule discharge line 7.

The manufacturer of the pump originally designed plug 50 to reduce the volume within the compression chamber in order to provide better self-priming characteristics for the pump. However, Applicant has discovered that the use of the reducing plug in the compression chamber increases the efficiency of microcapsule formulation; that is, a higher percentage of more completely formed capsules issue from the apparatus when the plug is in place. Applicant believes that the improved efficiency is caused by reflection of the pressure shock waves off of and about the various channels formed in the plug. It may also be that the confinement of the pressure shock waves to a smaller volume may increase the effective force generated on each unit volume of the dispersion by the shock waves. Alternatively, a combination of such effects or an as yet unrecognized additional mechanism may be at work. Because of the rapid re-cycling rate of the piston apparatus, the volume of capsules produced per unit time is not significantly reduced by the use of reducing plug 50.

As stated earlier, the exact physical mechanism by which capsules are formed by the above process is not known. It is believed that the application of the abrupt pressure change produces a pressure shock wave which directly causes the shell material to encapsulate the core material. On the other hand, the shear forces generated by the abrupt pressure change or by the pressure shock wave, or perhaps the local cavitation effects generated by the abrupt pressure change, the pressure shock wave, or shear forces may be responsible for capsule formation. Alternatively, it may be the release of the high pressure as the exit valve opens which causes, by one of the above mechanisms, the shell material to encapsulate the core material. The release of the pressure produces another abrupt pressure change which may cause cavitation bubbles to burst which in turn subject the dispersion to secondary pressure shock waves, shear forces, or thermal effects.

Whatever the actual underlying physical mechanism involved, it has been discovered that a single compressive stroke of the piston taking less than one second with the subsequent ejection of the fluid from the compression chamber forms capsules about the core material that was dispersed with the shell material. For purposes of this application, the term "abrupt pressure change" is intended to encompass the actual physical mechanism by which the capsules are formed including, but not limited to, pressure shock waves, shear forces, and cavitation effects.

Applicant has also discovered that the size of the capsules produced by the piston apparatus varies in inverse proportion to the air pressure supplied to pneumatic pump 22. The higher the air pressure supplied to pneumatic pump 22, the smaller the resulting capsule size becomes. As noted above, a change in the air pressure supply to pneumatic pump 22 causes the pump to perform differently in two different regards. First, due to the inherent pressure multiplying effect of the pump (resulting from the proportionate areas of the air piston in the pump mechanism and piston 20), the compressive force generated by the pump will increase or decrease with increasing or decreasing pressure. Secondly, due to the design of the pneumatic controls of the pump, the cycle rate of the pump increases or decreases with increasing or decreasing supply line air pressure. Thus, an increase in air pressure both increases the compressive force that the piston exerts as well as the cycling rate. Conversely, the increased cycle rate may be viewed as a decrease in the time it takes to complete one stroke cycle, or as a decrease in the time in which the compressive force is applied by the piston to the liquid medium containing the dispersion.

Applicant believes that, of these two effects, it is probably the increase in compressive force applied by the piston to the dispersion that is primarily responsible for the decrease in capsule size. Applicant arrives at this conclusion for the following reasons. Since the liquid medium containing the dispersion of shell and core materials is substantially incompressable, engagement of the free end of piston 20 on its compressive stroke with the fluid results in the virtually instantaneous abrupt pressure change being transmitted throughout the confined liquid medium as is well known to those experienced in the art. A slight advance of the piston, then, abruptly increases the pressure throughout the liquid medium. The substantially incompressable liquid would prevent further displacement of the piston since the pressure in the fluid would increase at every moment to match the piston's applied pressure. Thus, it is believed that the abrupt pressure change is a substantially instantaneous phenomena occurring as the piston begins its compressive stroke against the liquid medium.

The remainder of the piston stroke, after the initial application of the abrupt pressure change, serves to discharge the fluid through outlet check valve 4. Outlet check valve 4 will open the moment that the pressure within the chamber exceeds the valve's pressure setting. The abrupt pressure decrease to which the liquid is subjected occurs the moment that the check valve 4 opens. Thus, it would seem that the pressure increases and decreases within a very short period of time, much less than the time taken by the full downward stroke of the piston. Therefore, although the pneumatic pump motor 22 has a higher cycling rate at higher pressures, Applicant believes that the actual period during which the abrupt pressure changes are applied to the liquid medium remains a small fraction of that cycling time. While it remains possible that some unknown mechanism associated with a faster cycling rate may cause the decrease in capsule size with increase in cycling rate, Applicant believes that it is probable that the increased magnitude of the abrupt pressure change caused by the higher compressive force generated by the piston at higher driving air pressures is primarily responsible for the decrease in capsule size which is observed.

When capsules are produced by the above method and the apparatus of FIG. 3, much of the shell material is not utilized. Similarly, some core material remains unencapsulated. Also, the capsules which are formed may be incomplete, and those that are complete may have relatively thin malleable shells. Applicant has discovered that if the capsule containing medium exiting from check valve 4 is confined for a short period of time under conditions which induce turbulence, the capsules which are formed have thicker, more stable shell walls, and most of the shell material is used in creating the capsules. This may be accomplished by directing the discharge flow from compression chamber 18 into a narrow diameter exit tube 23 connected to exit valve 4. Due to the restricted diameter of exit tube 23, the flow rate of the capsule containing liquid through exit tube 23 will be increased. The restricted flow conditions on the exit tube side of check valve 4 may also work cooperatively with the spring in check valve 4, by creating a partial back pressure, to prevent check valve 4 from opening until sufficient pressure has been achieved in compression chamber 18. The longer residence time of the capsules in the shell containing medium yields a higher percentage of completed capsules having thicker walls. As noted, the quality and quantity of the capsules can be further increased by introducing turbulence into the flow of the capsule containing medium as it flows from exit tube 23.

Figure 5:
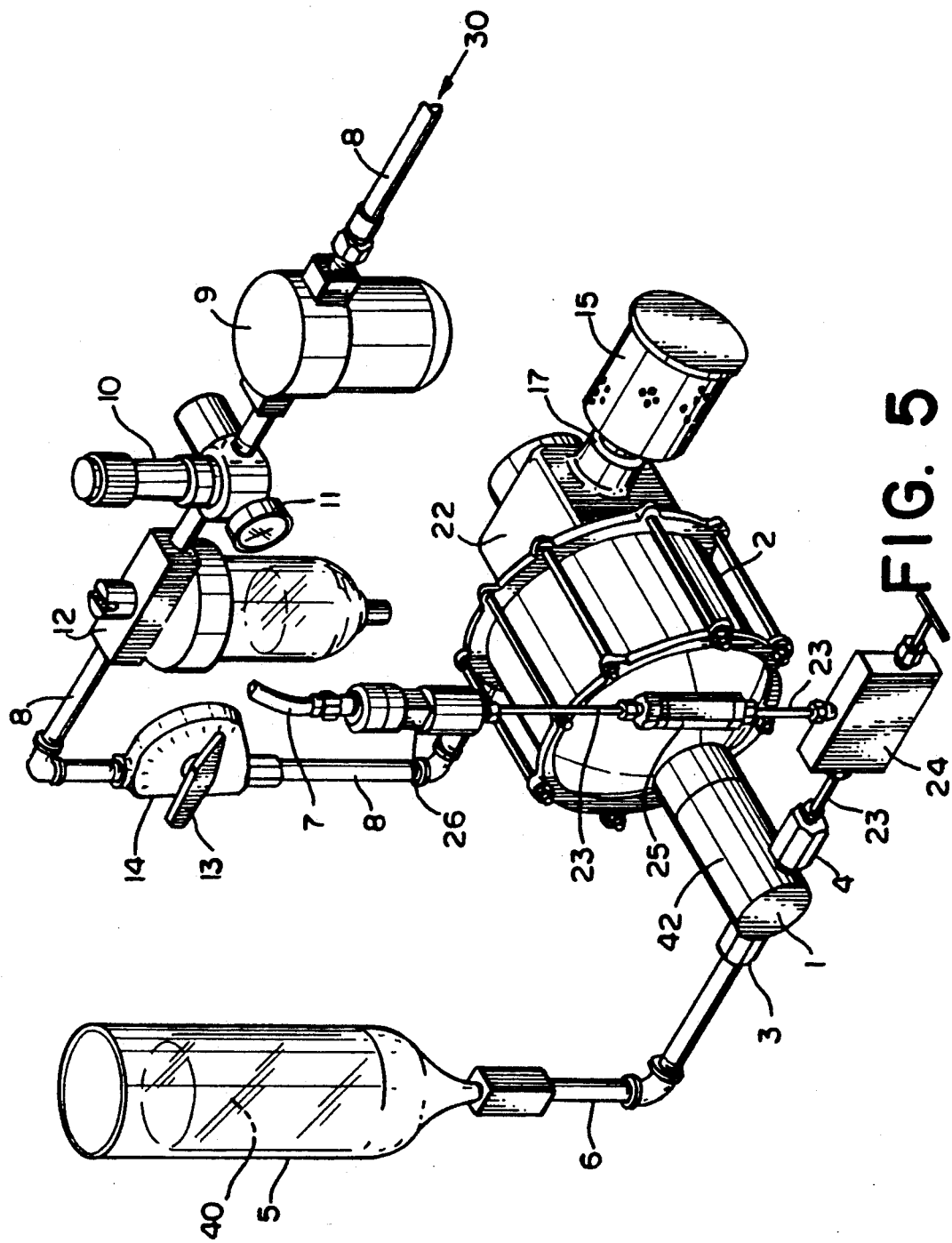
FIG. 5 shows the preferred embodiment of the piston apparatus.

FIG. 5 shows the preferred embodiment of the piston apparatus. Exit tube 23, having a diameter sufficiently reduced from that of compression chamber 18, is attached to exit valve 4. This reduced diameter exit tube 23 passes through right angle two way block valve 24. A clean out handle 43 allows removal of any accumulated debris within block valve 24. Exit tube 23 continues from block valve 24 to size-screening filter 25. Wire mesh screens (not shown) within size-screening filter 25 break up any large agglutinations of capsules. Filter 25 can be used to rupture capsules larger than a chosen size in order to narrow the size range of capsules produced. Typically 35 $\mu$ to 150 $\mu$ screens are used. Exit tube 23 continues from size-screening filter 25 to baffled chamber 26 in which turbulence is induced in the flow of the capsule-containing liquid medium.

Figure 6:
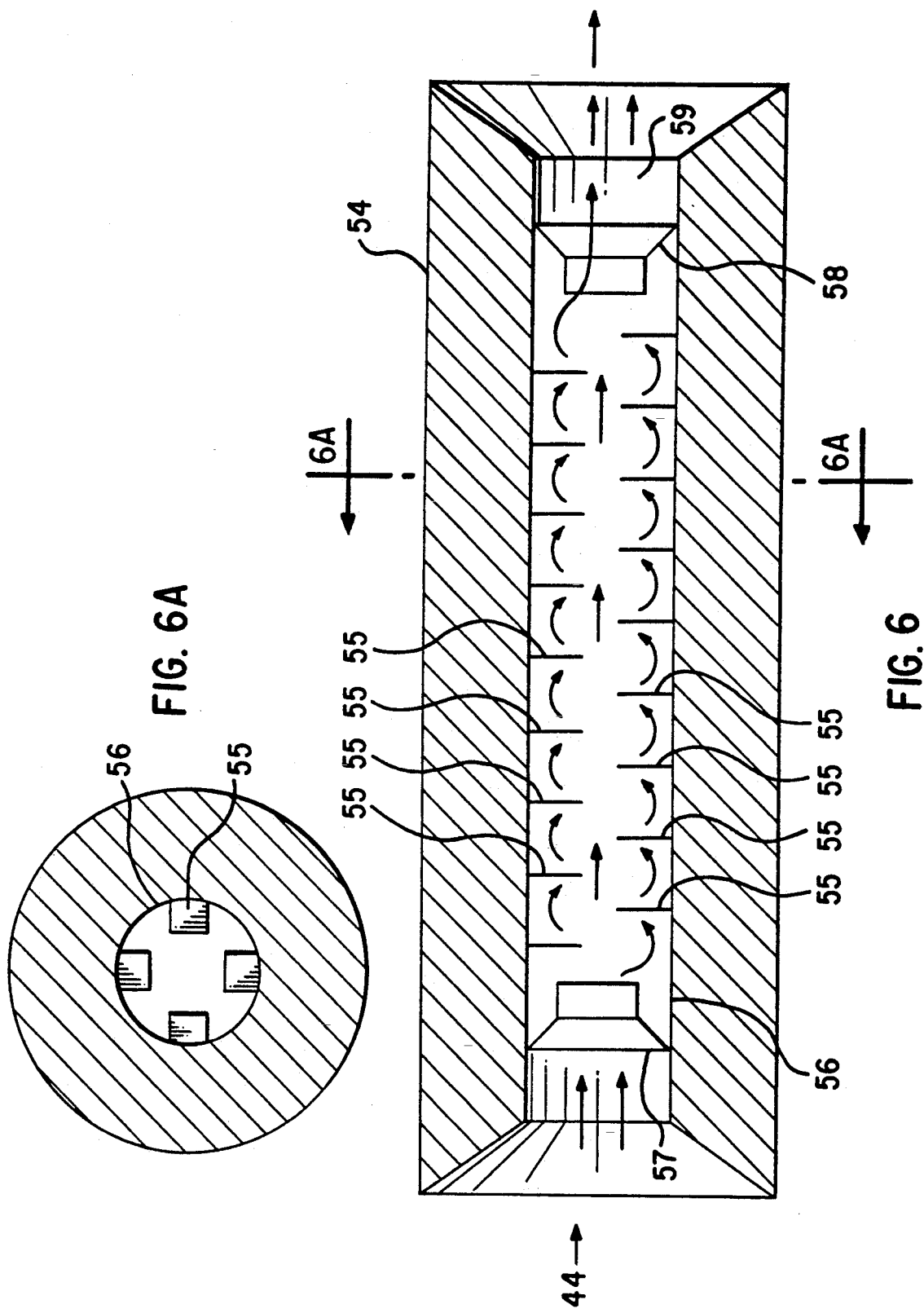

FIG. 6 shows a representational cross-section of baffled chamber 26. Baffled chamber 26 includes a section 57 of gradually decreasing diameter. There follows an inner chamber 56 having baffles 55 which interrupt and delay the flow of the capsule containing mixture 44 as it is pumped through chamber 56 and increase the turbulence of the flow. The arrows between baffles 55 are intended to indicate turbulent flow. Exhaust area 59 is connected to inner chamber 56 by a section 58 of gradually increasing diameter. As explained above, the turbulence created by the baffles tends to cause additional shell material, present in the mixture, to accrete upon the capsules, thereby increasing the total thickness of the capsule walls.

The baffled chamber 54 shown in FIG. 6 is sometimes called the "stabilization tube," because it is there that the capsules are stabilized. As the pump forces the capsule mixture through the stabilization tube, the fluid encounters a reduced diameter channel which increases the velocity of the fluid. As described above, the baffles in the tube cause turbulence which helps to cause unused shell material, which is floating freely within the mixture after the abrupt pressure change to accrete on capsules formed within the compression chamber. This has the effect of thickening the shell layer of the capsules by placing a second layer onto the initial shell layer.

The advantage of this two-layer construction is evident when the capsules were subjected to industrial stress, such as the pressure experienced in high-shear or high-speed pumps. The second shell layer tends to cover and correct the imperfections of the first shell layer. This layered shell structure has significant advantages over capsules made under prior art coacervation techniques, which produce only one shell layer. Single-layered capsules tend to have lesions, crevasses, and holes in the shell, and may be too weak to withstand the stress or shear experienced in many industrial processes.

The restricted diameter of the inner chamber 56 along with the baffles 55 presents an impediment to flow through chamber 54 which may produce a pressure drop across the length of chamber 54. The capsules are probably subjected to a decreasing pressure as they traverse the baffled chamber 26 from one end to another. By the time the capsules exit baffled chamber 26, the shell material has hardened sufficiently to enable the capsules to retain their shape and size.

Regardless of which variation of the present invention is used, the results are obtained much more rapidly than with any of the methods of the prior art. The speed of the process of the present invention makes it possible to encapsulate many compounds which cannot be encapsulated by regular liquid-phase methods. In conventional liquid-phase techniques, core materials which are soluble in the liquid medium often dissolve long before encapsulation can occur. But with the method of the present invention, many such soluble core materials can be encapsulated, because the encapsulation takes place before the materials have an opportunity to dissolve.

The turbulent flow generated in the preferred embodiment of the apparatus yields completed capsules having strong, thick, less soluble shells. Typically, 98% of the core material is encapsulated using the preferred embodiment of the invention with shell thicknesses comprising approximately 12 to 20% of the weight of the capsules. The total process time to create capsules with this apparatus from the starting dispersion is on the order of a few seconds. The dispersion is actually subjected to abrupt pressure change for less than one second, while the capsule-containing liquid medium has a residence time in the confinement and turbulence stage of only a few more seconds. Thus, a high through-put of capsule manufacture is possible with the method and piston apparatus of this invention.

Capsules produced by the method and apparatuses of this invention may be hardened by methods well-known in the prior art. These include pH changes, the addition of cross-linking chemicals, and heating to name a few. The hardening procedure chosen will depend upon the nature of the shell material which is used. The process of this invention does not limit the shell materials used or the hardening treatment which may be applied.

Figure 7:
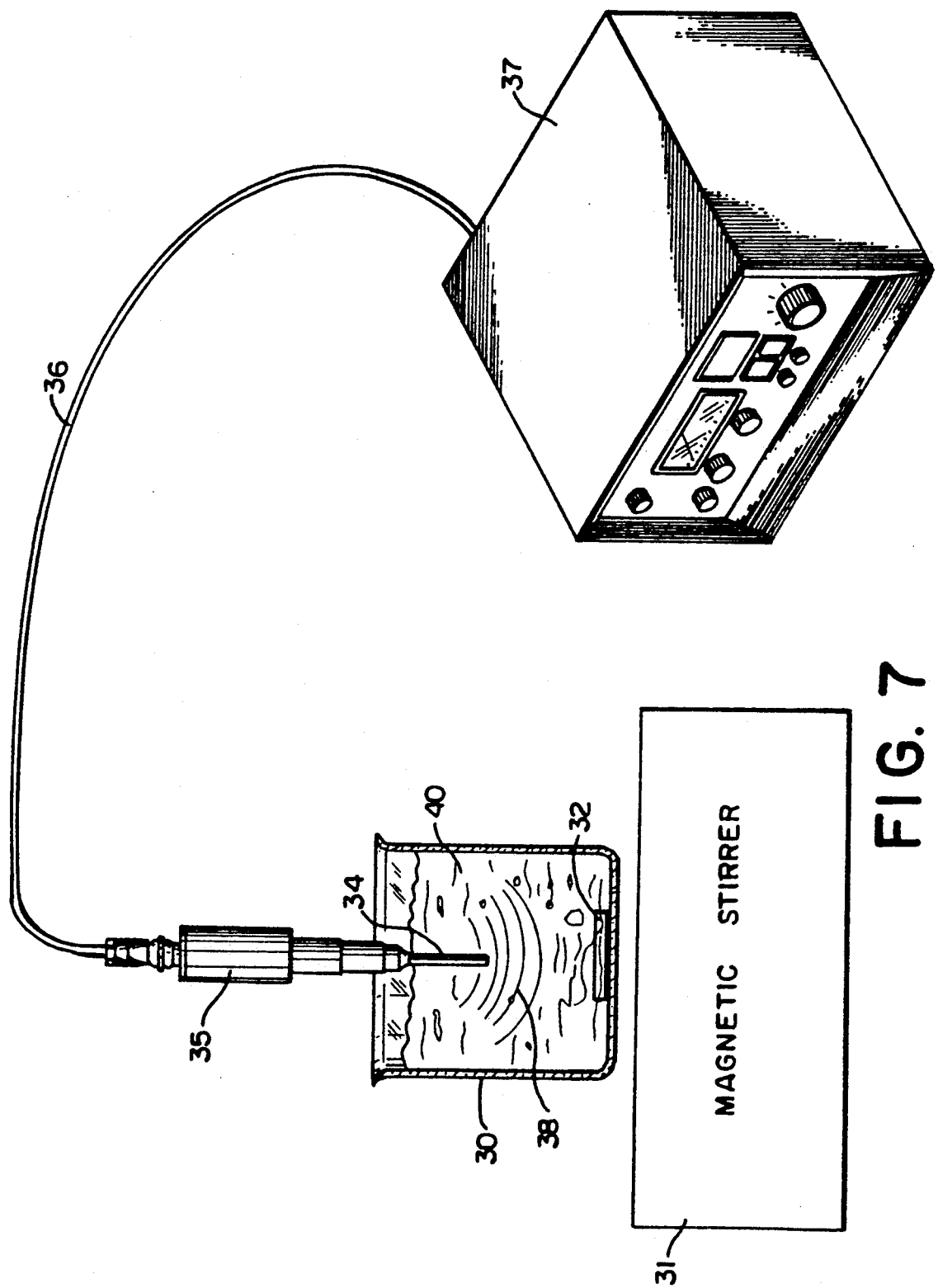
FIG. 7 shows an apparatus using ultrasound to make capsules.

A second apparatus for practicing the method of this invention is shown in FIG. 7. A treatment container 30 which may be heated if necessary, is supported on heater/stirrer 31 which is a combination heating element and magnetic stirrer. Magnetic stirrer bar 32 is located in container 30. Ultrasonic converter 35 is suspended so that horn 34 may be placed within container 30. Converter 35 is connected by power cable 36 to ultrasonic generator power supply 37.

To encapsulate materials with this ultrasonic apparatus, a dispersion 40 of core and shell material in a liquid carrier medium, which is prepared in the same manner as discussed above for use in the piston apparatus, is placed in treatment container 30. The core and shell materials are maintained in a dispersed state by the action of magnetic stirrer bar 32 which is driven by heater/stirrer 31.

Horn 34 of ultrasonic converter 35 is placed into the dispersion 40. Ultrasound 38 is applied to the dispersion 40. Typically, the dispersion 40 is subjected to the force of the ultrasound 38 for a period of ten minutes at an intensity level of 30 watts/(centimeter)$^2$. Stirring is continued during the application of ultrasound 38 to ensure exposure of all the shell and core material to the ultrasound. The ultrasound treatment causes capsules to form in the liquid medium.

Ultrasound is usually considered to work its effect through the creation of cavitation bubbles in the medium, although pre-cavitation oscillation in the medium occurs. The collapse of cavitation bubbles is accompanied by localized abrupt pressure changes which cause pressure shock waves, shear forces, and abrupt temperature spikes. As with the piston apparatus, Applicant is uncertain as to which of these postulated mechanisms, if any, is directly responsible for causing the encapsulation of the core material by the shell material. Using ultrasound, Applicant has discovered the effect, but does not know the mechanism. Once again, with the ultrasonic apparatus of this invention, the core material may be a solid, liquid, gas, or multiphasic compound and no limitation is placed on the nature of the shell material.

As with the piston apparatus, there are several variables which may be changed with the ultrasonic apparatus. For instance, the intensity of the forces generated by the ultrasonic transducer is determined by both the geometry and the volume of the vessel in addition to the characteristics of the liquid medium. Further, to ensure adequate exposure of the dispersion of core and shell material to the ultrasonic forces, continuous agitation throughout the period of ultrasonic encapsulation is required and is provided by the stirrer and stirrer bar. Applicant has discovered that, generally, longer duration exposures produce greater encapsulation efficiency and smaller capsules with the ultrasonic apparatus. However, capsule size is also a function of the intensity level of the ultrasound. Low intensity ultrasound produces larger capsules while higher intensity ultrasound produces smaller capsules.

An advantage of the ultrasonic apparatus is that several variables can be adjusted depending upon the nature of the core and shell materials as well as that of the liquid medium/carrier. In particular, the power and duration of exposure can be controlled and, where appropriate, even the frequency. For instance, the size of the capsules and their shell thickness may be adjusted by the proper selection of ultrasonic power and duration of exposure. Not only can the efficiency of the encapsulation be improved by longer exposure periods, but the heat generated in the medium during the processing by the ultrasound may be used with appropriate shell materials to harden the shells upon their formation or immediately thereafter. In addition, Applicant has discovered that a narrower range of capsule sizes is produced by the ultrasonic apparatus. The ability to control these various functions permits core materials to be encapsulated and other materials used as shells which otherwise, in the prior art, may not be utilized.

As will be discussed below, capsules may be recycled using the ultrasonic apparatus. For instance, larger capsules formed at lower ultrasonic power may be subsequently exposed to higher power ultrasound in order to reduce the size of the capsules. Similarly, additional shell layers of either the same or different shell materials may be applied. The ultrasonic apparatus also permits the formation of larger capsules using previously formed smaller capsules as the new core material.

Thus, the ability to vary power and timing of the process during ultrasonic encapsulation permits finer control of the encapsulation process. While the time to encapsulate a given volume of material is greater for the ultrasonic process, no turbulent stabilization tube is needed as has been found useful with the piston apparatus.

Figure 8:
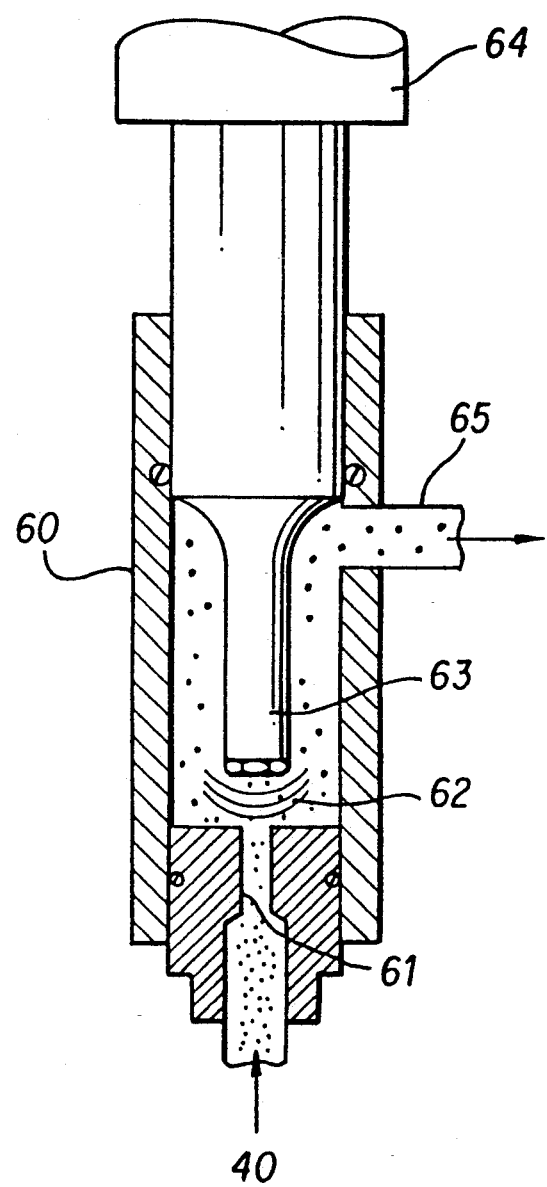
FIG. 8 shows another embodiment of an ultrasonic apparatus for making capsules.

FIG. 8 illustrates an alternative ultrasonic apparatus which permits continuous rather than batch encapsulation. Flow cell 60 has inlet 61 through which material is introduced and an outlet 65. The horn 63 of an ultrasonic converter 64 penetrates into the internal flow space of cell 60. To use the flow apparatus to encapsulate materials, a dispersion of core and shell material in liquid medium 40 is introduced into ultrasonic flow cell 60 through inlet 61. As the dispersion 40 flows into cell 60, it is saturated by ultrasound 62 emanating from horn 63 driven by ultrasonic converter 64. The capsules which are formed exit from outlet 65. An external pump (not shown) is used to circulate the dispersion through cell 60. The flow rate of dispersion 40 through cell 60 as well as the intensity of ultrasound 62 may be adjusted for optimum encapsulation conditions. Additional baffles (not shown) may be placed in the flow cell 60 to increase turbulence and the residence time of the capsules within the ultrasonic field. The capsules exiting from the system at 65 may be utilized as they are or recycled to the inlet 61 of the flow cell for further processing as will be discussed below.

Figure 9:
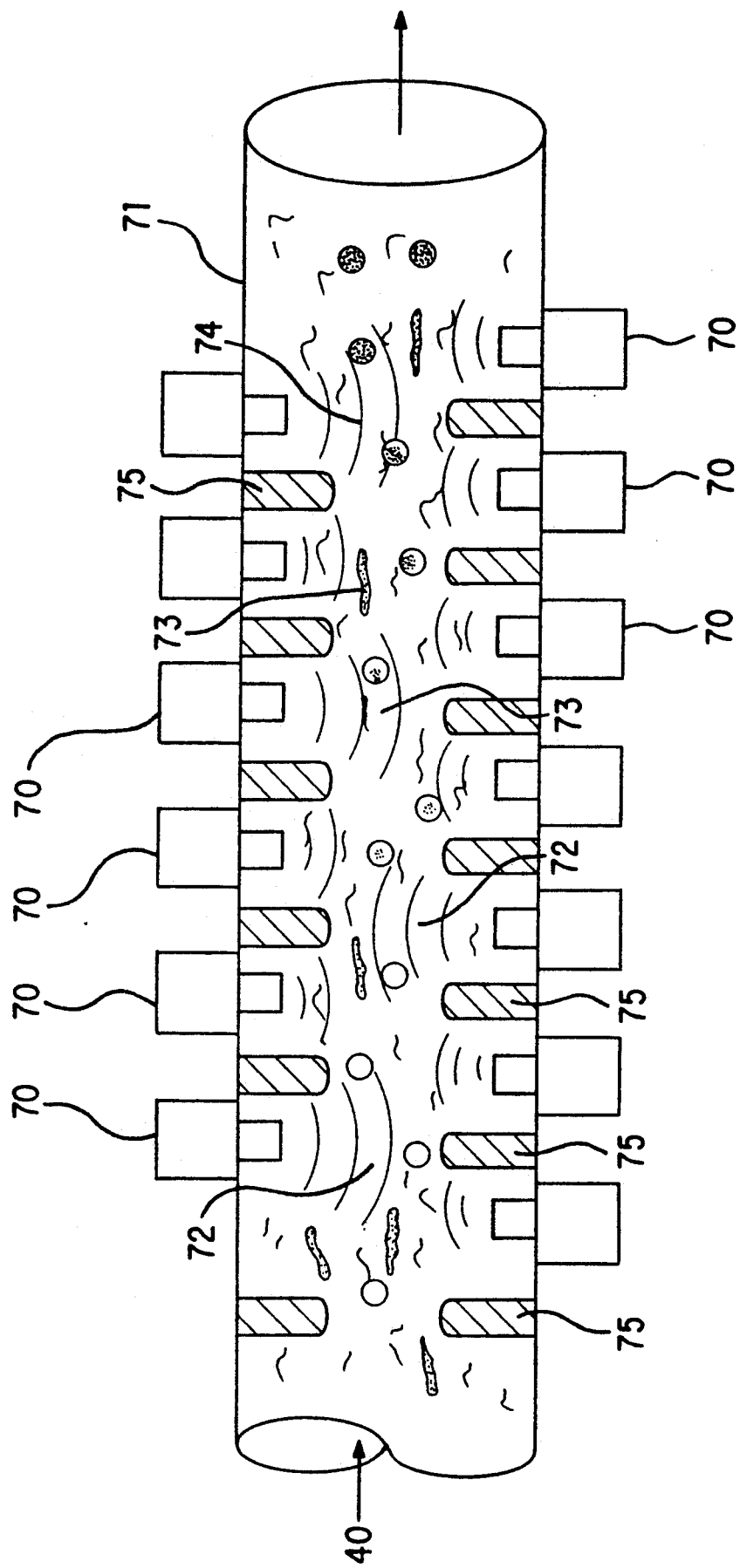
FIG. 9 shows another embodiment of an ultrasonic apparatus for making capsules.

FIG. 9 shows an alternative embodiment of a continuous ultrasonic encapsulation apparatus consisting of a long flow tube 71 along the sides of which are arrayed many ultrasonic converters 70 each of which has a horn 76 penetrating into the flow space of tube 71. Baffles 75 along the length of cell 71 may be provided to increase the turbulence within the cell to maintain the dispersion. To use this apparatus to encapsulate materials a dispersion 40 is pumped through cell 71. The array of ultrasonic transducers permits various power levels to be applied to the dispersion and capsules at different times in capsule formation (represented by the time course of the dispersion along flow cell 71). Thus, the power of ultrasound 72 applied by the earlier transducers may be of high intensity to create smaller capsules, while the power of the ultrasound 73 applied by later transducers may be of lower intensity in order to add additional shell layers without further size reduction. Finally, the power and frequency of ultrasound 74 applied by the last transducers may be adjusted to heat the liquid medium in order to harden the capsules. By lengthening the flow cell and adding additional transducers, the total time in which the dispersion and then the capsules are subjected to ultrasound may be increased.

Figure 10:
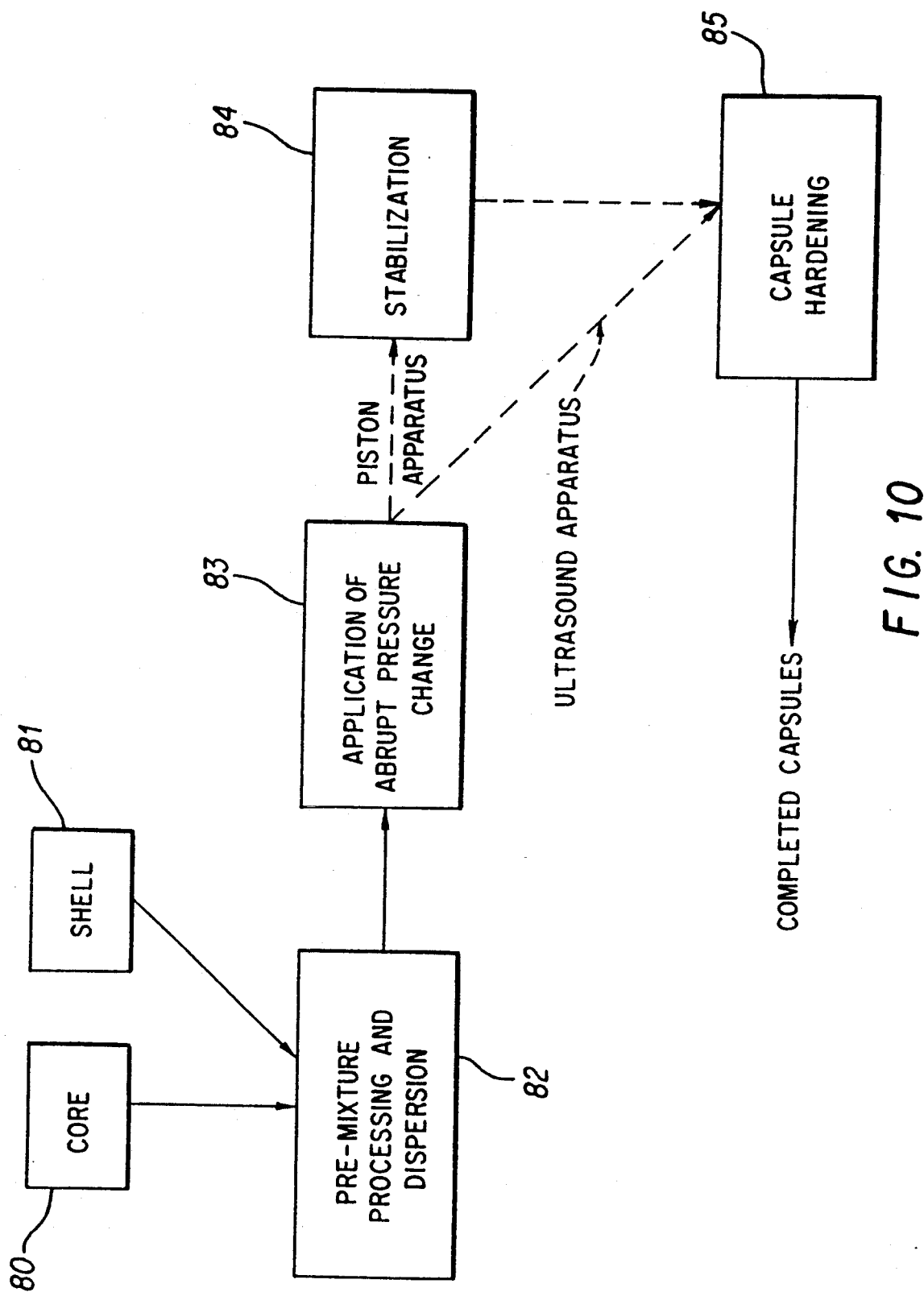
FIG. 10 is a block diagram illustrating the method of the process for manufacturing capsules.

FIG. 10 is a block diagram illustrating the method of the present invention in a process for capsule manufacture. In FIG. 10, core material 80 and shell material 81 are mixed together within a liquid medium indicated by block 82. Prior to mixing with the core, the shell material may have been prepared in its own solvent which is distinct from the liquid medium to be used during encapsulation, or the same liquid medium may be used throughout the process.

The core material may be added to the shell material at the time the shell material is prepared, or the core material may be added after the shell material is prepared. In most cases, the shell material requires separate preparation. For certain capsules, multiple core materials may be used.

The step represented by block 82, is known as the pre-mixture processing and dispersion stage. In this stage, the core and shell materials are dispersed in the liquid carrier medium. Any appropriate mixing device may be used, such as batch load stirring devices, motionless mixers, or fluidizing equipment. The mixture may or may not be heated during this stage, depending upon the materials employed and their chemical properties.

The agitation of the mixture is intended to produce a homogeneous mixture containing discrete particles of core material within a partially dissolved or bloomed shell material, all well-dispersed within the liquid medium. At this stage, the mixture is what has been called the "pre-mixture," and may be formed in a time as short as a few seconds, or as long as several hours, depending on the materials used. In the preferred method, a motionless mixer or static mixer is used which draws the pre-mixture ingredients through a long tube. Within the tube, a series of inserts produces turbulence which helps to mix the ingredients. The ingredients are drawn through the tube by a pump attached to one end of the tube. This method yields a very complete dispersion, and uses less energy and much less time than other methods.

The next step in the process is indicated in block 83. In step 83 the dispersion is subjected to an abrupt pressure change. The abrupt pressure change ma be generated by either the piston or ultrasonic device of this invention. In the piston apparatus, quantities of the pre-mixture are drawn periodically into the chamber, the dispersion is subjected to the action of the piston, and the resulting capsules ejected. The next batch of pre-mixture is then drawn into the chamber. In the ultrasonic apparatus the dispersion may be batch treated or pumped through an ultrasonic flow cell.

In some cases, the application of an abrupt pressure change is all that is required to form usable capsules. But, in other cases, the capsules which emerge from step 83 are unstable, and resemble the pre-formed capsules which result after the initial stage of coacervation. In these cases, additional processing is needed to thicken and harden the capsular wall to form a complete capsule. This is especially true of capsules produced by the piston apparatus.

Capsules formed very rapidly under the large abrupt pressure change generated by the piston apparatus may dissolve quickly if they are exposed to atmospheric pressure soon after formation. For instance, internal pressures within the capsules may be sufficient to expand and unravel the thin shell layer, causing the capsule to return to its original mixture state. To avoid this problem, capsules which are made within the piston apparatus are stabilized in step 84 by passage through baffled chamber which induces turbulence. The turbulence maintains a dispersion of the newly formed capsules and shell material so that loose shell material within the mixture will agglomerate onto the capsule and thicken the capsule wall. The stabilized capsules may then be hardened in step 85.

Capsules formed by the ultrasonic apparatus do not need an additional stabilization step since the newly formed capsules remain dispersed in the liquid carrier with the remaining shell material for a much longer period of time than do the piston generated capsules. Thus, ultrasonic formed capsules may be immediately hardened. Hardening step 85 may be effected by allowing the capsule containing mixture to sit for a time, or by subjecting the capsules to additional chemical or physical treatments, depending upon the nature of the materials used. Such treatments include temperature hardening, crosslink hardening through pH adjustments, use of chemical stabilizers, and radiation hardening.

The completed capsules typically leave hardening step 85 in the form of a slurry containing the liquid medium and the capsules. This slurry is known as the final post-mixture. Depending upon the application of the capsules, it may be desirable to provide the final product as a dry powder. In the latter case, dry powder separation and drying steps are required.

As stated above, a large magnitude abrupt pressure change tends to form smaller capsules and low magnitude abrupt pressure change tends to form larger capsules. Capsules having a diameter less than one micron may be produced by adjusting the magnitude of the abrupt pressure change in step 83.

More specifically, when capsules are formed by the abrupt pressure change, their size is determined by one or more of the following factors:

1. The initial size of the pre-formed capsules made in the mixing step or by a conventional liquid-phase encapsulation technique.
2. The initial size of the core material.
3. The magnitude of the abrupt pressure change applied by the apparatuses.
4. The characteristics of the shell material.

The capsules produced by the method and apparatuses of this invention may, themselves, be used in further processing by the method and apparatuses of this invention. Thus, capsules produced by a first pass through the apparatuses may be treated as the core material to be dispersed in the appropriate shell material for a second pass through the apparatuses. The various types of recycling possible can be broken down into two broad categories: 1) a subsequent recycling pass where the abrupt pressure change applied is of the same magnitude as was used to initially form the capsules; and 2) a subsequent recycling pass where the abrupt pressure change applied is of a different magnitude than was applied on the prior pass.

There are four principal reasons to recycle the capsules utilizing an abrupt pressure change of constant magnitude. The first reason is to increase the shell thickness of the capsule produced in the initial passage. In this case, on recycling, the capsules are dispersed within the same shell material as was used to form the capsules before applying the abrupt pressure change of the subsequent pass. Generally, the capsule that is produced in the second passage has approximately the same dimensions as the initial capsule, but a greater percentage of the capsule weight is in the shell. With some shell materials, upon microscopic examination the capsule shell can be seen to consist of two layers of shell material, one applied on top of the other. Weak spots in a first shell, which may undesirably reduce the strength of the capsule, may be corrected in this manner. Obviously, the capsules may be recycled under the same conditions as many times as desired to build up a desired wall thickness.

The second reason for recycling previously formed capsules with a constant magnitude abrupt pressure change is to change the composition of the exterior wall material. For instance, the first shell material may be non-porous to the core material but not have the structural integrity needed for the anticipated application. In such a case, the capsule produced by the first pass is dispersed with a different shell material prior to the second pass. The second application of the abrupt pressure change encapsulates the first capsule in a second shell of the different material. Obviously, this process can be repeated for as many different wall materials as desired and to build up the thickness of any chosen shell layer.

The third principal reason for recycling capsules at constant magnitude abrupt pressure change is to incorporate the capsules, along with an additional material, as the "core" of a new capsule. Usually, larger capsules result. To accomplish this, previously formed capsules are dispersed along with additional shell material in a liquid medium into which is also dispersed a second core material. This dispersion, when subjected to an abrupt pressure change, yields new capsules in which both the original capsules and the additional core material are encapsulated as the core with the shell of the new capsule enveloping both the older capsule and the additional core material. Once again, the outer shell layer may be of the same material or a different material than the shell material which was used to encapsulate the inner capsule. Obviously, these larger capsules may also be recycled, either to strengthen the outermost shell wall or to make multiple capsules within capsules. This technique is especially useful is producing time release capsules. Variations and permutations of these recycling processes should be evident to those skilled in the art. For instance, the capsules, whether derived from one or several passes, may have their shells hardened by methods well-known in the art before being recycled further.

The fourth reason to recycle capsules using a constant magnitude abrupt pressure change is to reduce the size of the resulting capsules. Often, multiple passes of a capsule, even at constant magnitude abrupt pressure change, yield capsules of much smaller size. The abrupt pressure change on the second pass through will generally reduce the size of the capsules, as the initially-formed capsules are not yet hardened and are still malleable.

There are several possible physical mechanisms which may explain the reduced size of the capsules. First, compression of the nearly completed capsule may drive out moisture present within the shell of the capsule, compacting the shell into a smaller thickness around the core, and reducing the total volume of the capsule. Secondly, if the core is a solid, the abrupt pressure change may fragment the capsule into small pieces. The residual shell material, though also broken during the fragmentation, may be still malleable enough to form another layer around the smaller particles. Thirdly, if the core material is a liquid, the abrupt pressure change may produce smaller dispersed droplets from the original capsule core. The shell material will tend to form a layer around the new droplets. After the capsules have reached the desired size, they may be hardened.

Recycling passes where the abrupt pressure change is not constant may also be used to modify capsule size. Passage of a previously made capsule, whose shell has not been hardened, through the apparatus a second time during which an abrupt pressure change is applied having a greater magnitude than the abrupt pressure change used to initially form the capsules, results in the capsules being reduced in size. Multiple passes of the capsules at an increased magnitude or at sequentially increasing magnitudes of the abrupt pressure change will reduce the capsule size even further. Capsules reduced in size by this method retain thick walls and show lower permeability of the shell to the core than capsules which have not been reduced in size. This reduced permeability is a phenomenon not known to the prior art where generally smaller capsules are known to be more permeable. Additional passes may be made where the abrupt pressure change is of a lower magnitude than used in the prior pass. For instance, it may be desired to add another shell layer without reducing the size of a capsule having a fragile shell wall which was formed by the prior pass. Obviously, combinations of cycles having lower magnitude abrupt pressure changes and higher magnitude abrupt pressure changes may be combined with the previously described recycling techniques to yield capsules with unique properties.

The ability to recycle capsules through the apparatuses of this invention is not limited to capsules initially formed by the method and apparatuses of this invention. Thus, capsules made by any one of the well known prior art techniques may be used as core material when dispersed with a suitable shell material in a liquid medium and processed by the method and apparatuses of this invention. Capsules only partially formed by prior art processes, such as coacervation, may have their formation completed by the method and apparatuses of this invention thereby shortening the total process time involved in completing the capsules.

In addition, in some cases, the shell material may not respond as desired to the abrupt pressure change, and will not properly encapsulate the core material. In such cases, a conventional liquid-phase encapsulation technique may be combined with application of the abrupt pressure change. In this method, encapsulation begins with a liquid-phase technique, such as coacervation, except that the liquid-phase process is not carried to completion. Instead, the pre-formed capsules are subjected to abrupt pressure change treatment to complete the encapsulation. This process is, therefore, known as a "combination technique."

"Pre-formed" capsules are defined as capsules having a very thin shell, wherein the shell occupies less than about 10% of the total volume of the capsule. Such pre-formed capsules are very malleable. They are unstable, and will fall apart if their shells are not thickened and hardened quickly. The pre-formed capsules may be made by a process such as coacervation or interfacial polymerization, or by any other methods which permit the formation of a capsule whose shell is neither thick nor hardened.

The combination technique thus includes two steps, namely a liquid-phase stage, wherein pre-formed capsules are made by a conventional method, and an abrupt pressure change stage, which completes the encapsulation process. The core and shell materials need to remain in the liquid-phase step only until such time as the capsules begin to form. After that, the encapsulation process may be completed with the method and apparatuses of this invention. Thus, the time spent in the liquid-phase step is typically only a fraction of the time that would be spent if the encapsulation was completed by a purely conventional process. Any conventional process for making the pre-formed capsules may be used as the first stage of the combination technique.

In the combination technique, the pre-formed capsule made according to the conventional process becomes the new core material which is encapsulated by application of an abrupt pressure change. Thus, the abrupt pressure change places an additional layer of shell material onto the capsule, increasing the thickness of the shell. If necessary, using the recycling method, the walls of the pre-capsules can be coated with several layers of shell material, approximating the second stage of a conventional coacervation process, as described earlier. However the use of the method and apparatuses of this invention to complete the encapsulation reduces the process time dramatically. With an abrupt pressure change, it is possible to complete the process in seconds instead of hours.

The combination technique described above is especially useful in cases where the dispersion of core and shell materials do not readily form capsules when subjected to an abrupt pressure change. For reasons which are not fully understood, certain core materials tend to disperse when subjected to an abrupt pressure change, and do not form cores that can be encapsulated. Other materials cannot be used as shell materials, for similar reasons. In these cases, one can overcome the problem by making preformed capsules with a conventional technique, and by completing the capsules with the method and apparatuses of this invention. The conventional liquid-phase technique is thus used as a "starter" in cases where direct application of an abrupt pressure change on the dispersion in the liquid medium does not work.

The abrupt pressure change stage of the combination technique approximates Stage 3 of the liquid-phase encapsulation processes described above. The capsule is sufficiently hardened to enable it to survive in the outside environment, and to release its contents only in the desired manner. The abrupt pressure change stage of the combination process is significantly speedier than conventional processes, since the application of an abrupt pressure change requires only a few additional seconds. Also, heat treatment and/or crosslinking chemicals may be used to produce a hardened shell at this final stage.

The magnitude of the abrupt pressure change needed for successful encapsulation varies significantly from one core and shell combination to another. The factors determining whether an abrupt pressure change will be effective are:

1. The viscosity and/or density differences between the core materials, the shell materials, and the liquid medium. Greater differences in viscosity and/or density yield more complete encapsulation by the method and apparatuses of the invention. If the viscosities and/or densities are too similar, encapsulation may not occur.

If the core material is a liquid droplet, the liquid core material must have a viscosity and/or density which differs from that of the liquid medium in which it is immersed. If the viscosity and/or density of the liquid core is too close to that of the liquid medium, the shell material, when subjected to the abrupt pressure change, tends to displace the liquid droplet and form globular spheres composed solely of the shell material. The liquid droplet core then dissolves and/or disperses within the liquid medium, and tends not to become encapsulated.

If the core material is soluble within the liquid medium, the application of an abrupt pressure change may cause formation of a capsule in such a short period of time as to enable the encapsulation to take place before the core disperses or is dissolved.

If the core is a gas bubble dispersed within the liquid medium, then the abrupt pressure change "recognizes" the bubble as a solid form and encloses the bubble with the shell material, thereby forming a gas-filled microcapsule.

The core material may be a liquid droplet which is not soluble in the liquid medium. If this is so, the abrupt pressure change will tend to form the shell material into an encapsulating coating around the liquid core droplet. The shell material then solidifies and seals the droplet, forming an encapsulated liquid.

2. The responsiveness of the shell and core materials to an abrupt pressure change. Materials which do not easily form capsules when subjected to an abrupt pressure change may require longer pre-capsule formation periods or a greater magnitude abrupt pressure change.

In general, any material which may be cast into a film state within a liquid medium is suitable for use as a capsular shell material in this invention. Shell materials also include those which are used in conventional liquid-phase encapsulation techniques, as well as other, more exotic materials which appear to function only when used with the method and apparatus of this invention. Examples of the latter substances are the synthetic elastomers listed in Table 3, as well as certain ceramic materials and ethylene vinyl acetate copolymers.

Many shell materials occur as a film when the material is dissolved within a solvent to the point where a thin, viscous membrane is formed within that solvent. These materials are not totally dissolved within the solvent. With colloid materials, such as gelatin, the materials are "bloomed" to the point where the materials pick up moisture or soak up the solvent and expand into a gelatinous film. In this case, the film may not be a single distinct form but a gelled mass.

In their film state, film forming shell materials are very responsive to the abrupt pressure change applied to the dispersion in the liquid medium. It is believed that the abrupt pressure change tends to force films within the liquid medium into a spherical shape and, while assuming a spherical shape, the shell material surrounds and seals whatever core particle is present within the liquid medium. Normally, the liquid medium which is present during the abrupt pressure change step is the same as the solvent in which the shell material is initially partially dissolved to form a film.

The viscosity of the film forming shell materials determines whether capsules will form under the influence of an abrupt pressure change. If too much of the shell material has been dissolved in the liquid yielding a highly viscous medium, the film will not respond to the abrupt pressure change and does not form capsules.

Examples of some liquids which can be used as the liquid medium/solvent are water, hexane, toluene, cyclohexane, and alcohols. Water is often used for colloid materials.

In the following examples, the piston apparatus was an air-powered hydraulic pump supplied by SC Hydraulic Engineering Corp., Los Angeles, Calif., the pump being designated as Model No. SC-10-600-8. The latter bump, with its associated check valves, essentially corresponds to the apparatus illustrated FIGS. 3, 4, and 5. However, for these examples the isolator attachment was not used.

The above-described pump is sold with inlet and outlet check valves, corresponding to check valves 3 and 4, respectively, in FIG. 4. These valves are also sold separately by the same company, under Model Nos. 10-450-24-SS and 10-450-23-SS, the latter valve having somewhat lesser stiffness (i.e. it opens at a somewhat lower pressure) than the former. The pump produces hydraulic pressure in the compression chambers of from 1,100 to 15,750 psi over a range of input pressures of 10 psi to 110 psi. The compressive pressure resulting from an inlet air pressure of 60 psi is rated, by the manufacture, to be 8,500 psi, on the assumption that the medium being compressed has a viscosity equivalent to that of water. Thus, the inlet air pressure is multiplied by the pump by a factor of approximately 140.

It was found that, in order to confine the dispersion within the compression chamber for a sufficient time to produce capsules, it was necessary to increase the spring tension in the output check valve. The necessary increase in spring tension was achieved by replacing the check valve, which was originally sold with the hydraulic pump, with a check valve designed to open at a higher pressure level. The replacement check valve was also obtained from SC Hydraulic Engineering, and was sold under Model No. 10-450-30-SS. The latter valve is one which is normally sold with another pump model, namely SC10-600-15, which is a similar pump having a higher pressure rating, namely from 1,900 to 26,000 psi, and having an approximate multiplier of about 233.

Thus, outlet check valve 4 of FIG. 4 was taken from a higher-pressure pump, and installed on the outlet end of the lower-pressure pump which was actually being used to produce the capsules in the Examples. Because the replacement check valve was designed to withstand more pressure, before opening, than the valve which was originally supplied with the pump, the replacement valve tended to remain closed longer than the original valve. The delay in opening of the outlet valve thus caused the dispersion to be confined somewhat longer within the compression chamber thereby subjecting it to an abrupt pressure change of greater magnitude. Eventually, the pressure in the chamber becomes sufficiently great to force the valve open, allowing the fluid to leave the chamber. Thus, it is believed that this modification of the pump insures that the abrupt pressure change produced by the piston will actually form capsules, and will not simply propel the fluids from the chamber.

It is also believed that the same results can be obtained by simply increasing the tension on the spring of the original check valve, without replacing the entire valve. A stiffer spring was found to approximate the action of the higher-pressure valve.

EXAMPLE 1

Combination of Partial Coacervation and Abrupt Pressure Change Processing

This Example shows the encapsulation of a flame retardant. The materials used in this experiment were:

a) 40 grams of Type 300 Bloom gelatin supplied by Kind and Knox Corp.;
b) 40 grams of gum Arabic supplied by Tic Gums;
c) 20 grams of Ethylcellulos supplied by Berol Industries;
d) 3.7 liters of tap water;
e) 360 grams of a bromochlorinated paraffin known as DD-8307, supplied by Dover Chemical.

In performing the procedure, the shell material was first treated to allow it to be used to form the capsular shell. The first four of the above-listed ingredients were mixed at room temperature under mild agitation, with a mixer operating at 100 R.P.M for 60 minutes. The result was a pre-condensate colloid wall material which is partially dissolved. A flame retardant known as DD-8307, which is a bromochlorinated paraffin in liquid form, in the amount of 360 grams, was added to the vessel containing the shell material pre-condensate under vigorous agitation. The mixture was heated to a temperature of 55° C. and then held at that temperature for 60 minutes. The mixture was then allowed to cool to 28° C. while agitation was continued, for about 10 minutes. Observation at this point revealed the presence of pre-capsules with an average particle size of 30-75 microns and containing a 5% shell material volume in relation to the fill material volume.

Then the mixture was introduced into the apparatus of FIG. 3 and capsules produced. The apparatus was set for a pressure at regulator 10 of 88 psi. Unless otherwise noted, all pressure readings mentioned herein are gauge pressure (psig). Since the pump speed was set at Level 3 (162 strokes per minute), the pump cycle took an estimated period of 0.37 seconds.

Examination of the capsules exiting from tube 7 at this point immediately after application of the abrupt pressure change, revealed capsules similar to those which would have been produced by ordinary coacervation techniques The capsules ranged in size from 5-15 microns, and now had an average shell volume of 12%. The capsules formed were observed to be spherical and complete, but the capsule shells were still malleable. Moreover, some loose shell material was observed within the mixture.

To help harden and solidify the walls of the capsules, a turbulence inducing baffle stabilization tube was attached. Capsules were then made which were observed to have a two-layer shell construction, when they exited the tube. The tube used in this Example was about six inches long. The length was found not to be critical for the materials used in this experiment.

In this Example, the capsules were hardened chemically after leaving the machine, by using formaldehyde to help cross-link the gelatin into a solidified form. Five grams of formaldehyde was used to accomplish this additional hardening The capsules finally exiting the apparatus were found to have a size range of 5-15 microns, with a wall material total volume of 25%. The efficiency of encapsulation, as measured by the percentage of fill material which was encapsulated at the conclusion of the process, was 98%.

The time required to obtain the completed capsules, using the starting materials listed above was 2 hours and 10 minutes, to form the pre-capsules under the partial coacervation stage, with just 4 seconds of pressurization processing, excluding the extra hardening step. However, when the experiment was repeated using coacervation alone, the time required to produce capsules of similar wall thickness was 7 hours and 35 minutes.

The following table compares the conventional coacervation process with the combination technique used in Example 1:

|  | Coacervation | Partial Coacervation With Abrupt Pressure Change |
|---|---|---|
| Capsule Size: | 10–60 u | 5–15 u |
| Process Time: | 7 hours, 35 min. | 2 hours, 10 min. |
| Wall Thickness: | 27% | 25% |
| Melt Temperature: | 265° C. | 275° C. |
| Efficiency: | 85% | 98% |
| Permeability in water (in 5 days): | 100% | 12% |

The above table shows that the present invention vastly increased the speed of encapsulation, and produced capsules having a marked decrease in permeability. The walls of the capsules produced according to the present invention were more dense, which partly explains why the capsules have a higher melting temperature. Also, the encapsulation efficiency was greatly increased.

In the following Example, Example 1 was repeated, with the goal of reducing the capsule size even further. The procedure of Example 2 could therefore be used where the completed capsules are too large for the desired industrial application, and where it is necessary to reduce their size.

EXAMPLE 2

Size Reduction Through Recycling

The procedure of Example 2 was repeated, producing capsules which were of the order of 5–15 microns in diameter, on the first pass through the system. But instead of the extra hardening stage involving additional physical or chemical treatments, the capsules were returned to the original compression chamber. On this second pass through the compression chamber, the pressure at regulator 10 was increased to 100 psi and the same speed setting of the pump was used. As explained in Example 1, it is believed that the cycle time of the pump was about 0.37 seconds.

The results were the same as those obtained in Example 1, except that the size of the microcapsules was reduced to about 3–10 microns. The higher pressure supplied to the pump inlet produced an abrupt pressure change of larger magnitude which seems to have compacted the capsules into a small volume, perhaps by reducing the void between the core material and the shell.

The capsules were then returned to the piston apparatus. On this pass, the capsules were further reduced in size to about 1–5 microns. The pressure at regulator 10 on the latter pass was still 100 psi, and the confinement time was believed to be the same since no change was made to the pump cycle frequency or the exit valve tension. Although the magnitude of the abrupt pressure change was unchanged, the capsules were nevertheless fractured into smaller particles, which were then recoated by the wall material. The volume occupied by the capsule wall remained nearly unchanged for each size reduction, and the permeability of the capsule wall also remained constant.

The following table summarizes the results of Example 2:

|  | Capsule Size |
|---|---|
| First pass: (88 psi) | 5–15 Microns |
| Second Pass: (100 psi) | 3–10 Microns |
| Third Pass: (100 psi) | 1–5 Microns |

EXAMPLE 3

Size Reduction by Recycling, with Constant Magnitude Abrupt Pressure Change

The goal of this experiment was to observe the effects of a constant magnitude abrupt pressure change on capsule size over multiple passes. The magnitude of the abrupt pressure change was unchanged from pass to pass.

Example 2 was repeated, using 3 passes through the piston apparatus. However, the pressure at regulator 10, on each pass, was maintained at the original level of 88 psi. The same speed setting for the hydraulic pump was used yielding a pump cycle time of 0.37 seconds. The same chemical formulation was used.

The results of the experiment are indicated in the table below. In each re-cycle pass, capsules were reduced in size, even at a constant regulator setting.

|  | Capsule Size |
|---|---|
| First Pass: (88 psi) | 5–15 microns |
| Second Pass: (88 psi) | 5–12 microns |
| Third Pass: (88 psi) | 3–8 microns |

EXAMPLE 4

Size Reduction Caused by Large Initial Abrupt Pressure Change

In this Example, Example 1 was repeated, except that the initial pressure at regulator 10 was increased to 150 psi. The same speed setting (Level 3) was used on the modified hydraulic pump system. The properties of the capsules were unchanged, except for their size and permeability. The process initially produced capsules having a diameter of about 1–5 microns, with a permeability of only 8% in water, during 5 days of exposure. Thus, where the abrupt pressure change was higher than in Example 2, the result was a smaller capsule having a shell which was more dense.

Small capsules tend to release their contents more rapidly than large capsules, due to their higher permeability. But, in this Example, the permeability of the small capsules was reduced by making their shells more dense. Thus, the present invention enables one to produce small capsules which release their contents more slowly.

EXAMPLE 5

Production of Capsules Without a Liquid-Phase Process

In this Example, Example 1, was repeated, except that the initial partial coacervation stage was omitted. The mixture was not agitated or heated. Instead, a motionless mixer was used to form microdispersions of the shell material, and this material was then mixed with the core material in another motionless mixer. A motionless mixer, also known as a static mixer, is characterized by a long tube with a helical element within. A fluid containing a mixture of chemical compounds is inserted in one end of the tube and pumped through. Interaction of the fluid with the helical elements causes the mixing or dispersion, as the mixture flows through the length of the tube.

In this Example, 40 grams of gelatin were combined with 40 grams of gum arabic, 20 grams of ethylcellulose, and 2.0 liters of tap water, in a mixing tank with mild agitation. The contents of the tank were then drawn, by an impeller pump, through a 2-foot long motionless mixer supplied by Koch Inc., while heat was applied to the mixing tube to raise its temperature to 100° C. This procedure yields a microemulsification of the shell material which is heated. The shell material emulsion was then added to 1.7 liters of tap water containing 360 grams of pre-dispersed DD-8307, which is an oily core material in liquid form. The combined mixture was then drawn through a second motionless mixer tube, of the same dimensions, at room temperature. The mixture exiting the second motionless mixer contained pre-capsules suitable for injection into the initial compressive chamber of the hydraulic pump apparatus. The same piston apparatus used in Example 1 was used here. The pressure at gauge 10 was set at 88 psi, and the same pump speed was used. These conditions produced capsules of identical physical parameters as were observed in Example 1. Only the process time was changed. The process time was reduced from 2 hours and 10 minutes to only 3 minutes and 17 seconds.

In Example 5, a microemulsion was produced with a simple mixing device, and coacervation was not used. The microemulsion stage required most of the process time of 3 minutes and 17 seconds. The actual formation of the capsules occurred during the abrupt pressure change step, which required less than one second.

The following table shows the effects of the magnitude of the abrupt pressure change on capsule formation:

| Inlet Pressure Setting (psi) Regulator 10 | Speed Setting Level on Device | Calculated Pump Cycle Time (sec.) | Capsule size (microns) |
|---|---|---|---|
| 88 | 3 | 0.37 | 5–15 |
| 150 | 3 | 0.37 | 1–15 |
| 88 | 6 | 0.23 | 3–10 |
| 150 | 6 | 0.23 | 0.5–3 |

The calculated pump cycle times are derived simply by dividing 60 seconds by the number of strokes per minute. These figures are only estimates; no direct measurements of cycle time were made.

The capsule size shown in the table is the initial capsule size after one pass through the compression chamber. The core material was DD-8307 bromochlorinated paraffin liquid, and the shell material was gelatin, gum arabic, and ethylcellulose. The table confirms that when the magnitude of the abrupt pressure change is increased, the resulting capsules are also smaller. It has also been found that similar size reductions occur for both liquid and solid core materials.

EXAMPLE 6

Adding Further Layers of Shell Material to an Exiting Capsule

This Example demonstrates a process for making capsules wherein there are competing considerations in the choice of the shell material. Suppose, for example, that a fungicide is to be encapsulated, but is found to have short shelf life, due to the low resistance to permeability of a gelatin-based shell material. A polymeric shell is useful in achieving the desired shelf life, but the polymer has the disadvantage that it repels the bacteria which digest the capsule and cause the release of its contents. The solution is to use a multi-walled capsule. In this case, the first wall is made of the polymeric material, and the second wall is made of gelatin which attracts the bacteria.

The multi-walled capsule was made in two stages. The first stage was the preparation of small capsules. A precondensate of urea-formaldehyde resin was first formed using 120 grams of urea mixed with 325 grams of 37% aqueous formaldehyde containing 15% methyl alcohol at room temperature. Triethanolamine was added, one drop at a time, to adjust the pH to 8. The mixture was then heated to 70° C., while keeping the pH below 8.5. After 1 hour of agitation, 600 ml of distilled water was added to the mixture, at room temperature. Then, 130.5 grams of the precondensate was further diluted with 200 ml of distilled water, producing a final polymeric solution to be used as the shell material.

Next, 10 grams of the above-described urea-formaldehyde shell solution was mixed with 40 grams of N-96 fungicide supplied by Diamond Shamrock Inc., in 400 ml of water, for 60 minutes, at a temperature of 25° C., under rapid agitation. Pre-capsules produced in this stage, which is generally referred to as an interfacial polymerization process, were between 10 and 30 microns in diameter. The emulsion was then delivered to the piston apparatus with regulator 10 providing a pressure of 82.5 psi. The cycle time was 0.37 seconds, for one pass, using the Level 3 speed setting on the pump. The abrupt pressure change produced capsules having a size between 8 and 20 microns, with an initial wall volume of 20%.

The second stage was the application of the second capsular wall. A mixture containing 40 grams of Type A, 300 Bloom gelatin was combined with 40 grams of gum arabic, and 20 grams of ethylcellulose, in 3.7 liters of tap water, and mixed at room temperature under mild agitation, for 60 minutes, to form a "bloomed" wall material solution. The capsules manufactured in the first stage were immersed in this new wall solution, under mild agitation, for 60 minutes while heat was applied at 65° C.

The new mixture containing the capsules made in the first stage was then subjected to an abrupt pressure change again. The pressure at regulator 10 on the second pass was 60 psi, with an estimated pump cycle time of 0.37 seconds, at a pump speed of Level 3. The second application of an abrupt pressure change caused a second shell to form around the first wall of the capsules, thereby creating capsules with two distinct wall layers.

The results of the two stages of this Example are summarized in the following tables:

| Stage 1 (Partial Interfacial Processing) | |
|---|---|
| Pre-capsule size | 10–30 microns |
| Initial Regulator 10 pressure | 82.5 psi |
| Speed Setting on Device | Level 3 |
| Calculated Pump Cycle Time | 0.37 seconds |
| Shell Material, wall layer #1 | Urea-Formaldehyde |
| Volume of Wall in relation to total volume of capsule by weight for wall layer #1 | 10% |

-continued

| | |
|---|---|
| Size of capsules after first pass | 8-20 microns |

Stage 2

| | |
|---|---|
| Shell material mixture | Gelatin |
| | Gum Arabic |
| | Ethylcellulose |
| Initial Regulator 10 pressure | 60 psi |
| Speed Setting on Device | Level 3 |
| Calculated Pump Cycle Time | 0.37 seconds |
| Size of final capsules | 6-20 microns |
| Total volume of wall in relation to capsule overall volume by weight | 18% |
| Volume of second wall layer | 8% |

The above table demonstrates that a second wall was formed around the initial polymeric shell, forming a capsule of two distinct wall layers.

EXAMPLE 7

Formation of Capsules Within Capsules

This Example shows a process for forming small capsules, and for encapsulating those capsules into larger capsules, producing what is known as a "multi-fill capsule." Such capsules are unusually strong, and release their contents very slowly.

The Example was performed in three stages. The first stage was the production of small capsules. Example 6 was repeated through its first stage, except that the regulator 10 pressure was raised from 82.5 psi to 100 psi. A pump speed setting of Level 3 was used giving a calculated pump cycle time of 0.37 seconds. The abrupt pressure change produced capsules having a size in the range of 5-12 microns, instead of the 10-30 microns of the first stage of Example 6.

The second stage was the preparation of the mixture for the new capsules. Stage 2 of Example 6 was repeated as described, except that a new core material was added to the shell mixture. This material was 400 grams of mineral oil. The new mixture now contained 100 grams of shell material and 400 grams of the new core material. The materials were immersed in 4 liters of tap water and stirred under mild agitation for 60 minutes. Heat was applied for the duration of the agitation, to a temperature of 65° C. This stage formed a second pre-mixture.

In the third stage, the capsules produced in the first stage were added to the second pre-mixture and stirred for 5 minutes under mild agitation with no further heat. Next, the new mixture was added to the piston apparatus with the pressure set at regulator 10 to 60 psi, and a speed setting of Level 3, giving a calculated pump cycle time of 0.37 seconds.

The resulting capsules were found to have several of the original small capsules encased within one large enclosure. The mineral oil was found between the inner shell layer, which was composed of urea-formaldehyde, and the outer shell layer, which was composed of gelatin, gum arabic and ethylcellulose mixture. The fungicide core material resided at the core center of the inner capsules. The size of the final multi-fill capsules ranged from 8 to 50 microns.

In the above Examples, a continuous method of capsule manufacture has been described. The invention may also be practiced with a batch process, in which one large quantity of a pre-mixture is subjected to an abrupt pressure change.

EXAMPLE 8

Production of Capsules Without a Liquid Phase Process and Without the Use of a Stabilization Tube In this Example no partial coacervation of the dispersion was used.

For this Example, in a large beaker 37.5 grams of gelatin, 300 bloom, were combined with 37.5 grams of gum arabic, 25 grams of ethylcellulose (F-411 Berol Chemi), and 3.333 liters of tap water. The mixture was stirred by an electric mixer while the mixture was heated on a hot plate to about 40° C. This procedure yielded a heated microemulsification of the shell material. The shell material was then allowed to cool down a few degrees before 400 grams of vegetable oil was added to the mixture under constant stirrings. The dispersion produced exhibited no signs of any capsule formation.

For this Example, the pneumatic pump 2 was rotated 90° C. so that the valves leading into the pump's compression head 1 appeared on the top and bottom of the compression head. The reservoir 5 was placed above the pump so that the dispersion could be fed gravitationally from the reservoir through valve 3 into compression chamber 18. A stirrer was placed in reservoir 5 to maintain the dispersion. Similarly, after an abrupt pressure change was applied, exit valve 4 could be opened and the compression chamber drained into a collection vessel located below exit valve 4. Both the entrance check valve 3 and exit check valve 4 of the preferred embodiment were removed and replaced with hand operated one-quarter turn ball valves.

Exit valve 4 was closed while entrance valve 3 was opened. The dispersion of core and shell material was permitted to drain into compression chamber 18 so that the chamber was filled. Then entrance valve 3 was closed. Pressure was set at regulator 10, at 60 psi and speed control 13 was set as level 3. One stroke cycle of the piston was applied to the dispersion. Exit valve 4 was opened and the capsule containing medium was allowed to drain into a collection container. Examination of the medium under the microscope showed that large capsules had formed. However, many of the capsules were not complete or only partially formed and there was apparently a good deal of both shell and core material remaining in the medium which had not formed capsules. Most of the shells of the capsules were fairly thin, although few formed thicker shells. It is therefore clear that application of a single abrupt pressure change produces encapsulation.

This experiment was repeated with the application of ten stroke cycles of the piston at the rate of one stroke per second. Examination of the resulting capsule containing medium showed many more capsules formed than had been formed with one stroke. Additionally, the capsules generally had thicker shells.

Example 9

Ultrasonic Encapsulation

A laboratory experiment is arranged according to the illustration provided in FIG. 7. The container 30 is a one liter glass beaker which is placed atop a magnetic stirring device 31. No heat was applied from the stirrer device during these experiments.

A blue dye and mineral oil mixture is made using 1.03 grams of blue dye, known as model number 2N from Orient Chemical Corp., and 43.96 grams of mineral oil, by stirring the ingredients in a separate beaker until the blue oil is completely mixed, producing 45 grams of blue oil which will serve as the core of the microcapsule.

A separate formulation consisting of 5.0 grams of gelatin (#300 bloom), 5.0 grams of gum arabic, 2.5 grams of ethylcellulose (#411 from Bermocell Corp.,) and 2.5 grams of karaya gum for a total weight of 15.0 grams of shell polymer mix.

250 ml of distilled water is applied to the beaker along with the blue oil and the shell mix. The beaker is placed atop the magnetic stirrer and a magnetic stir bar is placed into the beaker. The stirrer is activated and the stir bar rotates, generating turbulence within the dispersion.

An ultrasonic transducer probe is placed within the dispersion in the beaker at a distance of 2.0 inches above the magnetic stir bar. The ultrasonic device used was a Model #600 high intensity ultrasonic processor system produced by Sonics and Materials Inc. The device was set to generate 30 watts/cm$^2$ of ultrasonic intensity for a 10 minute exposure time, under constant transmission, no pulse. The system was activated and allowed to run the full 10 minutes time interval.

Sonic transmission waves were visible in the dispersion which continued to rotate under the transducer. The dispersion of oil and water first homogenized and changed to a lighter color. A temperature rise of nearly 15 (c) was recorded at the end of the 10 minute exposure interval.

A sample was then taken of the dispersion after ultrasound treatment and examined under microscope. Spherical capsules were observed with a size range of 10-30 microns. The shells were well defined forming a membrane layer surrounding the blue oil.

EXAMPLE 10

Re-Exposure To Ultrasound

The dispersion containing the capsules provided in Example 9 was placed back into the beaker and exposed to ultrasound for another 10 minute time interval at an intensity of 30 watts/cm$^2$. Examination of the capsules produced after this step revealed even smaller capsule sizes ranging from 1-2.5 microns. Capsule shells were still well defined however.

To determine that the spherical products observed under the microscope were actual capsules and not merely homogenous mixtures, the capsules were hardened by applying 0.45 grams of glutaraldehyde to the mixture and allowing the mixture to stir in the beaker for 60 minutes at room temperature. The spherical products were then filtered using a vacuum funnel system producing a blue-white power residue. The powder was then examined under a microscope and found to contain spherical capsules with a clear shell component layer. The final test was to crush the capsules. Upon exertion of finger pressure, the capsules ruptured, releasing the blue dyed oil. The conclusion was that the products produced by the ultrasound treatment were indeed microcapsules and not just microdispersions or a homogeneous mixture.

EXAMPLE 11

Interaction Between Hardening Agent And Ultrasound

Example 9 was repeated, but before the ultrasonic treatment was activated, the hardening agent, 0.45 grams of Glutaraldehyde, is stirred into the oil and water dispersion. The hardening agent is known to crosslink the natural polymers used in the shell mix, but generally does so with the application of heat over a period of several hours. In this experiment the effects of ultrasound directly upon the capsules and the effects of ultrasound directly upon the capsules and the hardening agent was tested. Ultrasound exposure was again set for 10 minutes at 30 watts/cm$^2$ intensity level, and the transducer activated. The observed temperature rise was 17(c).

At the end of the exposure the capsules were examined under a microscope and then filtered into a dry state. Only 10 minutes of ultrasonic treatment produced a hard capsule construction, definitely harder than the capsules produced without the hardening agent. The capsules were more difficult to rupture requiring more force to break them apart.

EXAMPLE 12

Use of Ureaformaldehyde Resin And Ultrasound

Example 9 was repeated, but instead of using 15 grams of natural polymers as the capsule shell material, 15 grams of ureaformaldehyde resin, known as URAC-180 from American Cyanamid, was used as a replacement. This aminoplast polymer resin is often used as a shell material in encapsulation and is known to crosslink either by catalyst agent or by thermal treatment.

The process was repeated using 25 watts/cm$^2$ ultrasonic intensity for 10 minutes. The capsules were again observed under microscope and then filtered by vacuum filter into a dry powder. Again the capsules had solidified into a hardened final form which was easily tested again by pressure breakage trial.

The capsules produced in this experiment were sized at about 30-50 microns, somewhat larger than the capsules made at higher intensity ultrasound.

EXAMPLE 13

Multiple Shell Layering Using Ultrasound

The capsules made in Example 9 were mixed/dispersed with another shell material, using a dissimilar polymer, and the new dispersion was exposed to a second cycle of ultrasound, to determine if multiple shell layering was possible using repeat ultrasound treatments. In this case, the same procedure was repeated as indicated in Example 9 with a first treatment of ultrasound at 30 watts/cm$^2$ intensity. This mixture containing capsules sized at 10-30 microns was left in the beaker and another 15 grams of urea-formaldehyde resin, URAC-180, was applied to the pre-treated capsule mixture. The new mixture was stirred for 15 minutes under rapid agitation, after which the ultrasonic treatment was begun again. The intensity level was the same in both ultrasound treatments and the duration of exposure was the same, 10 minutes.

After the second ultrasound treatment the capsules were filtered and examined under microscope. The resultant capsules were smaller than produced on the first pass. General observations were:

|  | PASS - 1 | PASS - 2 |
| --- | --- | --- |
| No. of Shell Layers | One | Two |
| Size Range | 10-30 Um | 1-15 Um |
| Efficiency of Encapsulation | 75% | 90% |
| Capsule Hardness | Moderate | Very Hard |

The capsules were both well formed but the natural polymer capsules after the first pass had not been chemically hardened. Additional exposure to ultrasound, in the second pass, produced an even harder capsule than had been accomplished when either the natural or the aminoplast shells were used singly.

EXAMPLE 14

Higher Intensity Ultrasound Treatment To Produce Smaller Microcapsules

Capsules using ureaformaldehyde resin shells from Example 12 were processed in the same manner as described in Example 12, except that the intensity of the ultrasonic transmission was set for 150 watts/cm$^2$ over a 10 minute exposure period.

The resultant capsules were observed to be in the sub-micron size range, approximately 0.10 to 0.50 microns. Optical examination was difficult at such size ranges but the filtered fine capsules were again able to remain in a stable state, not leaking any of the blue oil core, until crushed. This indicates that the shell material was again solidified into a complete enclosure by the ultrasound treatment.

These examples indicate the following features of the system:

1. Ultrasonic treatment can form capsules with stable shell membranes.
2. Such capsules can be formed through the use of ultrasound with both natural and synthetic polymer shell materials.
3. Higher intensity ultrasound can form smaller capsules.
4. Longer duration or repeat exposure can form smaller capsules.
5. Ultrasonic heat generation, caused by the process of cavitation, can provide a faster and more complete hardening of the shell material used in encapsulation by affecting a crosslinking or solidification of the shell.
6. By using repeated exposures, it is possible to provide multiple shell layers in resultant capsules, whereupon the shell layers can be composed of dissimilar materials.

I claim:

1. A method of making capsules, comprising the following steps:
   a. forming a dispersion of a core material and a shell material; and
   b. applying an abrupt pressure change to the dispersion, the abrupt pressure change being applied in a sufficient amount and for a sufficient time to cause capsules to form.

2. The method of claim 1 further comprising the additional steps, after step b, of:
   a. maintaining the capsule-containing dispersion under pressure; and
   b. allowing the pressure to dissipate gradually.

3. The method of claim 2 wherein the pressure dissipation step includes the step of inducing turbulence in the capsule-containing dispersion.

4. The method of claim 3 wherein the turbulence inducing step comprises the step of directing the capsule-containing dispersion through a baffled chamber.

5. The method of claim 1 wherein the abrupt pressure change is applied for a period of the order of one second or less.

6. The method of claim 1 wherein the step of forming the dispersion includes dispersing the core and shell materials in a liquid medium.

7. A method of making capsules, comprising the following steps:
   a. mixing a shell material with a solvent to form the shell material into a film state;
   b. forming a dispersion of a core material in the shell material; and
   c. applying an abrupt pressure change to the dispersion, the abrupt pressure change being applied in a sufficient amount and for a sufficient time to cause capsules to form.

8. The method of claim 7 further comprising the additional steps, after step c, of:
   a. maintaining the capsule-containing dispersion under pressure; and
   b. allowing the pressure to dissipate gradually.

9. The method of claim 8 wherein the pressure dissipation step includes the step of inducing turbulence in the capsule-containing dispersion.

10. A method of making capsules, comprising the following steps:
    a. dispersing a core material and a shell material in a liquid medium;
    b. agitating the dispersion until capsules being to form; and
    c. applying an abrupt pressure change to the dispersion, the abrupt pressure change being applied in a sufficient amount and for a sufficient time to complete the construction of the preformed capsules.

11. The method of claim 10 further comprising the additional steps, after step c, of:
    a. maintaining the abrupt pressure change treated capsule-containing dispersion under pressure; and
    b. allowing the pressure to dissipate gradually.

12. The method of claim 11 wherein the pressure reducing step includes the step of inducing turbulence in the capsule-containing dispersion.

13. A method of making capsules, comprising the following steps:
    a. providing a quantity of preformed capsules, the preformed capsules being present in a liquid medium;
    b. applying an abrupt pressure change to the liquid medium, the abrupt pressure change being applied in a sufficient amount and for a sufficient time to complete the construction of the preformed capsules.

14. The method of claim 13 further comprising the additional steps, after step b, of:
    a. maintaining the abrupt pressure change wave treated liquid medium under pressure; and
    b. allowing the pressure to dissipate gradually.

15. The method of claim 14 wherein the pressure reducing step includes the step of inducing turbulence in the pressure treated liquid medium.

16. A method of making capsules, comprising the following steps:
    a. forming a dispersion of a core material and a shell material;
    b. applying a first abrupt pressure change to the dispersion for a time sufficient to cause capsules to form; and
    c. applying a second abrupt pressure change to the dispersion to adjust the size of the capsules wherein the magnitude of the second abrupt pressure change is increased, if smaller capsules are desired, or decreased, if larger capsules are desired.

17. The method of claim 16, wherein the first abrupt pressure change applying step is preceded by the step of agitating the dispersion of core and shell materials until capsules begin to form.

18. A method of making capsules, comprising the following steps:
   a. forming a dispersion of a core material and a shell material;
   b. subjecting the dispersion to an abrupt pressure change, the abrupt pressure change being applied in a sufficient amount and for a sufficient time so as to form capsules; and
   c. hardening the capsules.

19. The method of claim 18, wherein the hardening step includes the following steps:
   a. maintaining the capsule-containing dispersion under pressure; and
   b. passing the capsule-containing dispersion through a baffled chamber, so as to reduce the pressure on the capsule-containing dispersion gradually, and so as to induce turbulence in the capsule-containing dispersion.

20. The method of claim 18 wherein steps a, b, and c are performed again following step c.

21. The method of claim 18 wherein the step of subjecting the dispersion to the abrupt pressure change is performed at least twice.

22. The method of claim 18 wherein step b is followed by the additional steps of:
   a. adding additional shell material to the capsule-containing dispersion: and
   b. again subjecting the capsule-containing dispersion to the abrupt pressure change.

23. The method of claim 18 wherein the hardening step comprises the step of treating the capsules chemically.

24. The method of claim 18 wherein the hardening step comprises treating the capsules with heat.

25. The method of claim 21 wherein the steps of subjecting the dispersion to abrupt pressure changes are performed with different magnitude abrupt pressure change.

26. The method of claim 22 wherein the steps of subjecting the dispersion to abrupt pressure changes are performed with different magnitude abrupt pressure changes.

27. The method of claim 22 wherein the adding step comprises adding a shell material which is different from the first shell material, whereby the resulting capsules have shells made of different materials.

28. A method of making capsules, comprising the following steps:
   a. forming a first dispersion of a first core material and a first shell material;
   b. applying an abrupt pressure change to the first dispersion, the abrupt pressure change being applied in a sufficient amount and for a sufficient time to produce capsules;
   c. forming a second dispersion with the capsules formed in step b, a second core material, and a second shell material; and
   d. applying an abrupt pressure change to the second dispersion, the abrupt pressure change being applied in a sufficient amount and for a sufficient time to produce capsules thereby producing capsules having at least two distinct cores.

29. The method of claim 28 further comprising after step d the additional steps of:
   a. maintaining the abrupt pressure change treated second capsule-containing dispersion under pressure;
   b. gradually decreasing the pressure on the abrupt pressure change treated second capsule-containing dispersion; and
   c. inducing turbulence in the abrupt pressure change treated second capsule-containing dispersion.

30. A method of making capsules, comprising the following steps:
   a. forming a first dispersion of a first core material and a first shell material;
   b. agitating the first dispersion, until capsules begin to form;
   c. forming a second dispersion with the capsules formed in step b, a second core material, and a second shell material; and
   d. applying an abrupt pressure change to the second dispersion; the abrupt pressure change being applied in an amount sufficient and for a time sufficient to produce capsules
thereby producing capsules having at least two distinct cores.

31. The method of claim 30 further comprising after step d the additional steps of:
   a. maintaining the abrupt pressure change treated second capsule-containing dispersion under pressure;
   b. gradually decreasing the pressure on the abrupt pressure change treated second capsule-containing dispersion; and
   c. inducing turbulence in the pressure shock wave treated second capsule-containing dispersion.

32. An apparatus for making capsules comprising:
   a. a means for forming a dispersion of a core material and a shell material; and
   b. means for applying an abrupt pressure change to said dispersion, said means applying an abrupt pressure change in a sufficient amount and for a sufficient time to cause capsules to form.

33. The capsule making apparatus of claim 32 further comprising:
   a. means for maintaining the capsule-containing dispersion under pressure; and
   b. means for allowing the pressure to dissipate gradually.

34. An apparatus for making capsules comprising:
   a. means for storing a dispersion of core and shell materials;
   b. means for generating an abrupt pressure change;
   c. a compression chamber, fluidly connected to storing means, the compression chamber also being connected to means for generating an abrupt pressure change within the chamber, said chamber having inlet and outlet check valves, said check valves having sufficient stiffness to confine the dispersion within the chamber while the abrupt pressure change is being applied to the dispersion, for a time sufficient to produce capsules; and
   d. means for conveying the capsule-containing dispersion out of the chamber.

35. The apparatus of claim 34 further comprising:
   a. means for maintaining pressure on the capsule-containing dispersion, the pressure maintaining means being connected to the conveying means; and b. means for gradually reducing the pressure on the capsule-containing dispersion, the pressure reducing means being connected to the conveying means.

36. The apparatus of claim 35 wherein the pressure reducing means comprises a tube having baffles disposed within the interior of the tube.

37. The apparatus of claim 35 wherein the pressure dissipating means includes a channel having a gradually decreasing diameter.

38. The apparatus of claim 39, wherein the channel includes means for increasing the turbulence of flow of the capsule-containing dispersion.

39. The apparatus of claim 38 wherein the turbulence increasing means includes a plurality of baffles positioned within the path of flow of the capsule-containing dispersion.

* * * * *